United States Patent

Rogalski et al.

[11] 4,024,272
[45] May 17, 1977

[54] TETRACYCLIC COMPOUNDS

[75] Inventors: Werner Rogalski; Richard Kirchlechner; Jürgen Seubert; Rudolf Gottschlich; Rosmarie Steinigeweg; Rolf Bergmann; Helmut Wahlig; Joachim Gante, all of Darmstadt, Germany

[73] Assignee: Merck Patent Gesellschaft mit beschrankter Haftung, Darmstadt, Germany

[22] Filed: Aug. 26, 1975

[21] Appl. No.: 607,803

[30] Foreign Application Priority Data

Sept. 6, 1974 Germany .............. 2442829

[52] U.S. Cl. .............. 424/275; 260/562 A; 260/574; 260/607 A; 260/609 R; 260/621 R; 260/622 R; 260/623 R; 424/257; 424/283; 260/279 R; 260/289 R; 260/306.7 R; 260/307 A; 260/328; 260/335; 260/327 TH; 260/345.2; 260/515 A; 260/515 M; 260/515 P; 260/516; 260/518 A; 260/518 R; 260/519; 260/521 N; 260/521 P; 260/521 R; 260/521 S
[51] Int. Cl.² .............. C07D 335/16
[58] Field of Search .............. 260/328; 424/275

[56] References Cited

UNITED STATES PATENTS 3,988,468   10/1976   Rogalski et al. .............. 424/275

Primary Examiner—Cecilia M. S. Jaisle
Attorney, Agent, or Firm—Millen & White

[57] ABSTRACT

Tetracyclic compounds of the formula

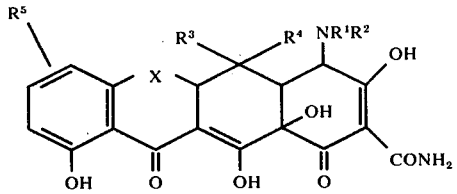

wherein $R^1$, $R^2$, $R^3$ and $R^4$ each are H or alkyl, $R^5$ is H, F, Cl, Br, $CF_3$, OH, alkyl, alkoxy, $NO_2$, $NH_2$, alkylamino, dialkylamino or acylamino and X is O, S, SO, $SO_2$, NH, N-alkyl or N-acyl, alkyl and alkoxy in each case being of 1–3 carbon atoms and acyl in each case being of 1–4 carbon atoms, with the proviso that when $R^5$ is methoxy and X is a sulfur atom, $R^5$ is in the 8- or 9-position only, and their physiologically acceptable acid addition salts, possess broad spectrum antibacterial activity, including tetracycline-resistant Gram-positive and Gram-negative organisms.

20 Claims, No Drawings

TETRACYCLIC COMPOUNDS

BACKGROUND OF THE INVENTION

This invention relates to novel tetracyclic compounds.

In a composition aspect, this invention relates to tetracyclic compounds of the general Formula I

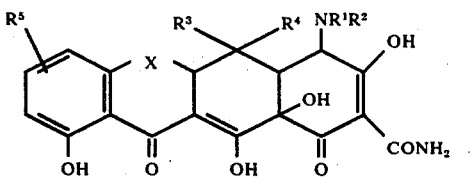

wherein $R^1$, $R^2$, $R^3$ and $R^4$ each are H or alkyl, $R^5$ is H, F, Cl, Br, $CF_3$, OH, alkyl, alkoxy, $NO_2$, $NH_2$, alkylamino, dialkylamino or acylamino and X is O, S, SO, $SO_2$, NH, N-alkyl or N-acyl, alkyl and alkoxy in each case being of 1–3 carbon atoms and acyl in each case being of 1–4 carbon atoms, with the proviso that when $R^5$ is methoxy and X is a sulfur atom, $R^5$ is in the 8- or 9-position only, and their physiologically acceptable acid addition salts.

In other composition aspects, this invention relates to pharmaceutical compositions comprising in unit dosage form a novel tetracyclic compound of this invention in admixture with a pharmaceutically acceptable carrier.

In further composition aspects, this invention relates to novel intermediates for the production of the novel compounds of this invention.

In process aspects, this invention relates to processes for the production and use of the compositions of this invention.

DETAILED DISCUSSION

The compounds of Formula I can possess various stereo-chemical configurations. Specifically, they can possess the same stereochemical configuration at the carbon atoms $C_{4a}$ and $C_{5a}$ of the tetracycline structure as the tetracyclines prepared by the action of microorganisms in which the hydrogen atoms are in the syn-position, i.e., the "natural configuration", as in Formula I$a$.

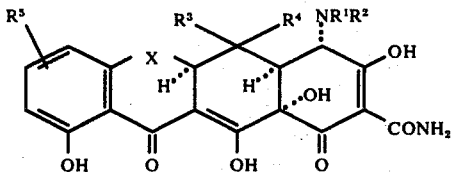

However, the carbon atoms $C_{4a}$ and $C_{5a}$ can bear hydrogen atoms in the anti-position and thus possess an "unnatural configuration". Compounds having this "unnatural configuration" are designated "5a-epi-compounds" hereinafter. Those compounds of Formula I which possess the "natural" configuration (Formula I$a$) and the corresponding 5a-epi-compounds are preferred. It will be apparent that there are further possibilities for isomerism at $C_{(4)}$, $C_{(5)}$ and $C_{(12a)}$, and all of the epimeric compounds which are thus possible are contemplated and included in generic Formula I.

"6-Thia-tetracycline" as used herein means 4-dimethylamino-1,4,4,$a$,5,5$a$,6,11,12a-octahydro-3,10,12,12a-tetrahydroxy-1,11-dioxo-6-thianaphthacene-2-carboxamide with the stereo-chemistry indicated in Formula I$a$. Analogously, "6-oxa-tetracycline" and "6-aza-tetracycline" are the corresponding 6-oxa- and 6-aza-naphthacene-2-carboxamides.

In the compounds of Formula I, $R^1$ to $R^4$ are preferably H or methyl. In particular, $R^1$ and $R^2$ are preferably identical and are preferably H or methyl and $R^3$ and $R^4$ are preferably H. However, $R^1$ to $R^4$ can also be ethyl, n-propyl, isopropyl, n-butyl, isobutyl, sec.-butyl and tert.-butyl.

Contemplated classes of compounds and their acid addition salts within the scope of Formula I are those wherein:
a. $NR^1R^2$ is $NH_2$;
b. $NR^1R^2$ is N(alkyl)$_2$, especially $N(CH_3)_2$;
c. $R^3$ and $R^4$ both are hydrogen atoms or methyl groups in the syn configuration, especially those of (a) and (b);
d. $R^3$ and $R^4$ both are hydrogen atoms in the anti-configuration, especially those of (a) and (b);
e. X is O, especially those of (a), (b), (c) and (d);
f. X is S, especially those of (a), (b), (c) and (d);
g. X is NH, $NCH_3$ or $NCOCH_3$, especially those of (a), (b), (c) and (d);
h. $R^5$ is 7-Cl or 7-$(CH_3)N_2$, especially those of (a), (b), (c), (d), (e), (f) and (g);
i. $R^5$ is 8-OH or 8-$OCH_3$, especially those of (a), (b), (c), (d), (e), (f) and (g);
j. a compound of (a), (b), (c), (d), (e), (f) or (g) in free base form;
k. a compound of (a), (b), (c), (d), (e), (f) or (g) in acid addition salt form, preferably the hydrochloride.

Accordingly, in a preferred aspect, this invention relates to compounds of Formula I in which at least one of $R^1$ to $R^4$ has one of these preferred values.

In a process aspect, this invention relates to a process for the production of compounds of Formula I and of their physiologically acceptable acid addition salts.

a. a compound otherwise corresponding to the general Formula I but wherein at least one hydroxyl or amino group is present in a functionally modified form, is treated with solvolyzing or hydrogenolyzing agents; or
b. a compound of the Formula II

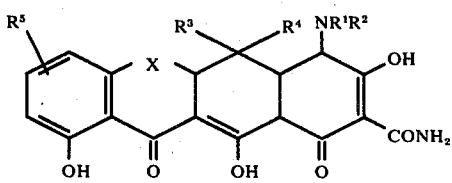

wherein $R^1$ to $R^5$ and X have the values given above, is treated with a hydroxylating agent; and, optionally thereafter, one or more of the $R^1$, $R^2$, $R^5$ and/or X groups in the resulting product are converted, by treatment with a solvolyzing, alkylating, acylating, oxidising, nitrating and/or reducing agent, into an $R^1$, $R^2$, $R^5$ and-/or X having another value and/or the group $NR^1R^2$ is epimerized, and/or a thus-produced base of Formula I is converted, by treatment with an acid, into one of its physiologically acceptable acid addition salts, or a thus-produced salt is converted by treatment with a base into a free base of Formula I.

In other respects, the preparation of the compounds of Formula I is carried out in accordance with methods which are in themselves known, such as are described in the literature (for example, in the standard works, such as Houben-Weyl, Methoden der Organischen Chemie (Methods of Organic Chemistry), Georg-Thieme-Verlag, Stuttgart) especially in the literature which is concerned with the chemistry of the tetracyclines, and in particular under the reaction conditions which are known and suitable for the reactions mentioned.

If desired, all the starting materials for the preparation of the compounds of Formula I can also be formed in situ, in such a way that they are not isolated from the reaction mixture but are reacted further directly to give the compounds of Formula I.

The starting materials are novel. They can be prepared by total synthesis, analogously to the methods known from the literature.

Among those starting materials which otherwise correspond to Formula I but wherein at least one hydroxyl or amino group is present in a functionally modified form, preferred are those in which the 4-amino group and/or the 10-hydroxyl group is functionally modified.

Others, for example, are those in which the $NH_2$ radical of the carbamoyl group in the 2-position is functionally modified.

The 4-amino group is preferably modified in the form of an acyl or thioacyl derivative or of an imino-ether or imino-thioether derived therefrom. Accordingly, it is preferably present in the form of one of the groups $-NR^1-CY-R^6$ or $-N=C(YR^7)-R^6$, wherein $R^6$ is, in particular, H, SH, alkylmercapto of 1–4 carbon atoms, benzylmercapto, alkyl of 1-10 carbon atoms, unsubstituted phenyl, benzyl, phenoxymethyl or phenoxypropyl, or a corresponding phenyl, benzyl, phenoxymethyl or phenoxypropyl radical which is monosubstituted or disubstituted by alkyl of 1–4 carbon atoms, OH, temporarily protected OH, $CH_2OH$ optionally with a temporarily protected OH group, $NO_2$, $NH_2$, alkylamino, dialkylamino, hydroxyalkylamino, acylamino, halogen, COOH, COO-alkyl, $CONH_2$ or CONH-alkyl, wherein Y is an oxygen atom or a sulfur atom and $R^7$ is alkyl, the alkyl groups preferably being of up to 4 carbon atoms and the acyl groups preferably being of up to 7 carbon atoms. "Temporarily protected" OH groups are preferably in the form of $R^8O$ radicals, wherein $R^8$ is alkyl, alkoxymethyl or acyl, preferably of up to 5 carbon atoms in each case, tetrahydropyranyl and carbobenzoxy or, especially, benzyl. If the 10-hydroxyl group is functionally modified, it is preferably in the form of a $R^8O$ radical, wherein $R^8$ has the values given above.

If the carbamoyl group in the 2-position is functionally modified, it is preferably present in the form of the radical $-CONHR^9$, wherein $R^9$ is alkyl of 1–6 carbon atoms, especially tert.-butyl.

The solvolytic splitting of a functionally modified hydroxyl and/or amino group must, of course, be carried out under such mild conditions that other groups in the molecule, for example, the carbamoyl group in the 2-position, are not also attacked. However, this is easily possible in accordance with the instructions given in the literature. The solvolysis is preferably effected with the aid of an acid, for example a mineral acid, such as hydrochloric acid, hydrobromic acid, sulfuric acid or phosphoric acid, an organic carboxylic acid, such as acetic acid, or a sulfonic acid, such as methanesulfonic acid or p-toluenesulfonic acid. Lewis acids such as $BF_3$ or $BBr_3$ are also suitable for splitting functionally modified hydroxyl groups. The solvolysis can be carried out in the presence or absence of an inert solvent. Examples of suitable solvents are water, alcohols, such as methanol, ethanol or isopropanol, ethers, such as diethyl ether, tetrahydrofuran (THF) or dioxane, chlorinated hydrocarbons, such as methylene chloride, chloroform or trichloroethylene, hydrocarbons, such as benzene, or mixtures of these solvents. It is also possible to use an excess of the acid, for example, acetic acid, as the solvent. As a rule, the solvolysis is carried out at temperatures of 0° to 150° C., preferably 20° to 100° C.

Specifically, for example, an N-substituted carbamoyl group in the 2-position, preferably a $-CO-NH-$tert.-butyl group, can be converted into the group $-CONH_2$ by treatment with HCl, HBr, sulfuric acid or phosphoric acid. The use of HBr in acetic acid at temperatures between 20° and 80° C. is particularly advantageous.

Hydrolysis of an amide group in the 4-position is effected particularly easily when $R^6$ is alkyl or phenyl substituted at least in the o-position, in which case the substituent on the phenyl nucleus should facilitate the hydrolysis by means of an "adjacent group effect". The hydrolysis can then take place even under very mild conditions, for example, in a weakly acid medium using dilute acetic acid, methanol, ethanol, THF and dioxan being preferred, as well as water, as additional inert solvents.

A particular procedure for eliminating acyl or thioacyl groups at the N atom in the 4-position is to convert them into the corresponding imino-ether or imino-thioether groups. This is preferably effected using alkylating agents, such as methyl iodide, dimethyl sulfate, oxonium salts, such as triethyloxonium tetrafluoborate, or fluorosulfonic acid alkyl esters, such as fluorosulfonic acid methyl ester or fluorosulfonic acid ethyl ester. Preferably, the alkylating agent and the amide or thioamide to be split are allowed to act on one another in one of the inert solvents mentioned, for example, in methanol, methylene chloride or mixtures of these solvents. It is preferably for a base, such as $KHCO_3$ or 1,8-bis-dimethylaminonaphthalene, to be present to neutralize the acid which is formed The imino-ether or imino-thioether is then split by the action of one of the acids mentioned and best of all by means of dilute hydrochloric acid at temperatures of about 0° to 50° C.

Hydroxyl and/or amino groups which are protected by groups which can be split off hydrogenolytically can also be liberated hydrogenolytically. Thus, for example, O-benzyl, N-benzyl or carbobenzoxy groups can be removed hydrogenolytically or the imino ethers or imino-thioethers mentioned, in which $R^6$ is a phenyl group, optionally substituted as indicated above, can be split hydrogenolytically.

The hydrogenolysis is preferably carried out in the presence of one of the conventional metal catalysts, for example, in the presence of platinum, palladium, nickel or cobalt. These catalysts can be present as finely divided metals, as oxide catalysts (for example, platinum oxide) or on supports (for example, platinum or palladium on charcoal or palladium on calcium carbonate). The hydrogenolysis is appropriately carried out at pressures from 1 to 100 atmospheres and at temperatures from −80° to +150° C. in the presence of one of the indicated solvents, preferably at pressures from 1 to 10 atmospheres and temperatures from 20° to 50° C. in methanol or ethanol.

Compounds of Formula I can also be obtained by hydroxylation of compounds of Formula II in the 12a-position. A suitable hydroxylating agent is oxygen, which is preferably used in the presence of a metal or metal salt catalyst (for example, $PtO_2$ or $CeCl_3$), under alkaline conditions, for example, in the presence of a buffer solution, and in the presence of one of the inert solvents mentioned, preferably methanol, ethanol, THF, dimethylformamide (DMF) and/or water. The reaction temperatures for the hydroxylation are preferably from 0° to 50° C., especially from 20° C to 30° C., and the reaction times are from 5 minutes to 10 hours, preferably from 10 minutes to 3 hours.

If desired, in the resulting product of Formula I, one or more of the $R^1$, $R^2$, $R^5$ and/or X groups can be converted by solvolysis, alkylation, acylation, oxidation, nitration and/or reduction into one or more other $R^1$, $R^2$, $R^5$ and/or X groups having another value given above.

In particular, it is possible solvolytically to split off a 6-acyl group and/or to split a 7-, 8- or 9-acylamino group, and/or to alkylate a 4-amino or 4-monoalkylamino group and/or an unsubstituted 6-aza group or a 7-, 8- or 9-hydroxyl group, a 7-, 8- or 9-amino group or a 7-, 8- or 9-monoalkylamino group, and/or to acylate an unsubstituted 6-aza group and/or a 7-, 8- or 9-amino group, and/or to oxidize a 6-thia group, and/or to nitrate a compound of Formula I, wherein $R^5$ is H, and/or to reduce a nitro group in the 7-, 8- or 9-position to the amino group or to reduce a 6-sulfoxide group to the thio-ether, and/or hydrogenolytically to replace a chlorine or bromine atom in the 7-, 8- or 9-position by a hydrogen atom.

A resulting acylamino compound of Formula I ($R^5$ = acylamino and/or X = N-acyl) can be split by treatment with a solvolyzing agent, preferably a hydrolyzing agent, the corresponding amine of Formula I ($R^5$ = $NH_2$ and/or X = NH) being formed. The splitting is effected under the conditions indicated above, for example, using HBr/acetic acid.

A resulting hydroxy compound of Formula I ($R^5$ = OH) or a resulting primary or secondary amine of Formula I ($R^1$ and/or $R^2$ = H and/or X = NH and/or $R^5$ = $NH_2$ or alkylamino) can be alkylated by treatment with an alkylating agent to give the corresponding alkoxy compound or to give the corresponding secondary or tertiary amine.

Examples of suitable alkylating agents are alkyl halides, such as methyl chloride, methyl bromide or methyl iodide or ethyl chloride, ethyl bromide or ethyl iodide, dialkyl sulfates, such as dimethyl sulfate or diethyl sulfate, alcohols, such as methanol or ethanol, in the presence of Raney nickel, or the corresponding aldehydes or ketones, such as formaldehyde, acetaldehyde or acetone, in the presence of a reducing agent, for example, in the presence of hydrogen and a metal catalyst, or of formic acid, or in the presence of a complex metal hydride, such as sodium cyanoborohydride. Preferred solvents for the alkylation are alcohols, such as methanol or ethanol, ether-alcohols, such as 2-methoxyethanol or 2-ethoxyethanol, ethers, such as THF or dioxane, or amides, such as DMF.

The alkylation can also be carried out in two stages. For example, a resulting primary amine can first be acylated, for example, converted into the corresponding formyl derivative using the mixed anhydride of formic acid and acetic acid (for example in formic acid in the presence of sodium formate).

The resulting acyl derivative can then be converted into the desired secondary amine, for example, by catalytic hydrogenation under the conditions indicated above.

In order to alkylate a phenolic hydroxyl group, it is also possible to use diazoalkanes, especially diazomethane, preferably in the presence of an inert solvent, for example, an ether, such as diethyl ether or dioxan, at temperatures from about 0° to 30° C.

Acylation of resulting primary (I, $R^5$ = $NH_2$) or secondary (I, X = NH) amines to give the corresponding acylamino compounds is preferably effected with carboxylic acids of 1–4 carbon atoms, or with derivatives thereof. Examples of suitable carboxylic acid derivatives are carboxylic acid esters, anhydrides (for example, acetic anhydride) or halides, such as chlorides, bromides or iodides (for example, acetyl chloride, bromide or iodide). An excess of the carboxylic acid derivative can be used as the solvent or the reaction is carried out in the presence of an inert solvent, such as benzene, toluene, THF, dioxane or chloroform. When carrying out the acylation, it is preferable to add a base, preferably a tertiary amine, such as pyridine or triethylamine, which in excess can also serve as the solvent. As a rule, the acylation is carried out at temperatures from about −20° to +50°, preferably from 0° to 30° C.

Oxidation of resulting 6-thiatetracyclines (I, X = S) to give the corresponding sulfoxides (I, X = SO) is preferably effected with hydrogen peroxide and also with peracids, or electrolytically under relatively mild conditions and at relatively low temperatures (about −80° to +100° C.). If, on the other hand, it is desired to obtain the sulfones (I, X = $SO_2$), the same oxidizing agents can be used under more vigorous conditions and/or in excess as well as at, as a rule, higher temperatures. In these reactions, the customary inert solvents can be present or absent. Examples of suitable inert solvents are water, aqueous mineral acids, aqueous alkali solutions, alcohols, such as methanol or ethanol, esters, such as ethyl acetate, ketones, such as acetone, carboxylic acids, such as acetic acid, nitriles, such as acetonitrile, hydrocarbons, such as benzene, and chlorinated hydrocarbons, such as chloroform or $CCl_4$.

A preferred oxidizing agent is 30% aqueous hydrogen peroxide. This leads to the sulfoxides when used in the calculated amount in solvents such as acetic acid, acetone or ethanol at temperatures between about −20° and 100° C. and to the sulfones when used in excess at higher temperatures (approximately up to 150° C.), preferably in acetic acid or in a mixture of acetic acid and acetic anhydride.

It is also possible to oxidize resulting sulfoxides under more vigorous conditions to give the sulfones, in which case it is not necessary to isolate the sulfoxides.

Resulting compounds I, in which $R^5$ is H, can be nitrated according to methods which are in themselves known to give the corresponding nitro compounds (I, $R^5$ = $NO_2$). Preferably, the 7- and/or 9-nitro derivatives are formed. Suitable nitrating agents are, above all, nitric acid and salts thereof, potassium nitrate in liquid HF preferably being used. In addition, it is also possible for inert solvents to be present, for example, chlorinated hydrocarbons, such as chloroform, methylene chloride or tetrachloromethane. In general, the reaction is carried out at temperatures from about −80° to +100° C., preferably from −10° to 30° C.

Catalytic hydrogenation, above all, is suitable for the reduction of nitro groups to amino groups, for example, under the conditions indicated above for hydrogenolysis, especially on a noble metal catalyst such as palladium-on-charcoal in methanol or ethanol at room temperature and normal pressure. In particular, metals (for example, iron or zinc) with acids (for example, hydrochloric acid or acetic acid) or $SnCl_2$ are also suitable for the reduction of nitro groups.

Sulfoxides of Formula I (X = SO) can be reduced, for example, using triphenylphosphine in $CCl_4$, to give the corresponding 6-thiatetracyclines (I, X = S).

In resulting chlorine or bromine compounds of Formula I ($R^5$ = Cl or Br), the halogen atoms can be replaced hydrogenolytically by hydrogen, for example, under the conditions indicated above for hydrogenolysis, preferably using hydrogen on a noble metal catalyst such as palladium on charcoal in methanol or ethanol in the presence of a base, such as triethylamine, at room temperature and normal pressure.

It is, of course, possible and in some cases advantageous, to combine two or even more of the process measures described with one another.

Thus, for example, the amino group in the 4-position and the hydroxyl group in the 10-position can simultaneously be liberated hydrolytically from corresponding derivatives by using HBr, HI or $BF_3$ as the agent. Furthermore, it is possible, for example, simultaneously to carry out hydrogenolytic splitting of a benzyloxy group, present on the $C_{(10)}$ atom, and reductive alkylation of an amino group in the 4-position, in the presence of hydrogen and a catalyst.

If desired, in a resulting product or a product mixture (for example, a mixture of stereoisomers) of Formula I, the group $NR^1R^2$ in the 4-position can be epimerized, in particular, according to methods which are known from the literature to give the "natural" configuration. This is effected, for example, by treating the product or the mixture, which contains undesired epimers, with an alkaline earth metal salt, such as calcium chloride, in a buffered solution at pH values from about 8 to 10, for example, in aqueous n-butanolic solution in the presence of ethanolamine at temperatures from about 20° to about 150° C., preferably at the boiling point.

A base of Formula I can be converted into one of its physiologically acceptable acid addition salts by treatment with an acid. Acids which can be used for this reaction are inorganic acids, for example, sulfuric acid, nitric acid, hydrogen halide acids, such as hydrochloric acid, hydrobromic acid or hydroiodic acid, and phosphoric acids, such as orthophosphoric acid, as well as organic acids, especially aliphatic, alicyclic, araliphatic, aromatic or heterocyclic monobasis or polybasic carboxylic acids or sulfonic acids, such as formic acid, oxalic acid, malonic acid, succinic acid, pimelic acid, fumaric acid, maleic acid, tartaric acid, malic acid, gluconic acid, citric acid, methanesulfonic acid or ethanesulfonic acid, ethanedisulfonic acid, 2-hydroxyethanesulfonic acid, benzenesulfonic acid, p-toluenesulfonic acid or naphthalene-monosulfonic acids or naphthalene-disulfonic acids (for example, naphthalene-1- or -2-sulfonic acid or naphthalene-1,5- or -2,6-disulphonic acid).

The starting compounds for the production of the novel compounds of this invention can be prepared, e.g., analogously to the process described in German Offenlegungsschrift No. 1,543,221, whose disclosure is incorporated by reference.

For example, a phenol, thiophenol or arylamine of Formula III

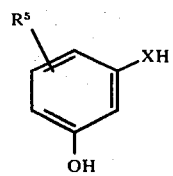

wherein $R^5$ and X have the values given above and the hydroxy group also can be functionally modified, i.e., in the form of an $R^8O$-group as defined above, is added to a dialkyl glutaconate. The resulting adduct is saponified to yield a 3-aryl-X-glutaric acid of Formula IV

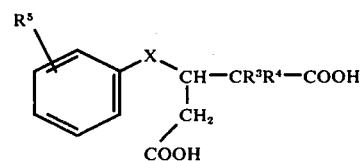

wherein $R^3$, $R^4$, $R^5$ and X have the values given above and the hydroxy group also can be functionally modified. This compound is cyclized and subsequently the remaining carboxyl group is, preferably stepwise, reduced to an aldehyde group to yield an aldehyde of Formula V

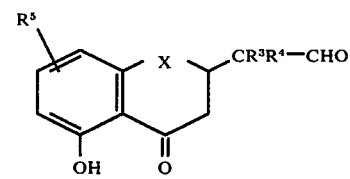

wherein $R^3$, $R^4$, $R^5$ and X have the values given above and the hydroxy group also can be functionally modified.

The aldehyde of Formula V can be condensed with an unsaturated azalactone (such as a 2-aryl-2-oxazoline-5-one) or with an unsaturated thioazalactone (such as a 2-aryl-2-thiazoline-5-one) to yield a compound of Formula VI

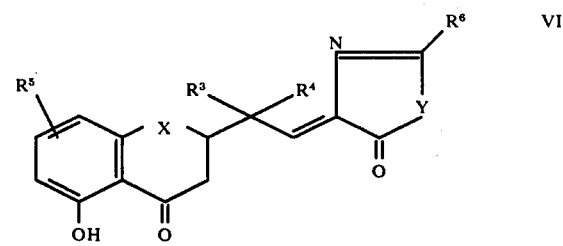

wherein $R^3$ to $R^6$, X and Y have the values given above and the hydroxy group can also be functionally modified.

This product is reacted with an acetonedicarboxylic acid monoester monoamide of Formula VII

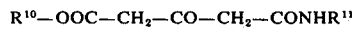

$R^{10}-OOC-CH_2-CO-CH_2-CONHR^{11}$      VII wherein $R^{10}$ is alkyl of 1–6 carbon atoms, and $R^{11}$ is H or alkyl of 1–6 carbon atoms, to give an intermediate of Formula VIII

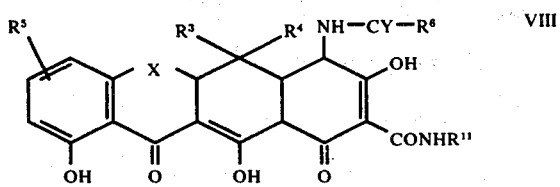

wherein $R^3$ to $R^6$, X and Y have the values given above and the hydroxy group in the 10-position can also be functionally modified. The compounds of Formula VIII can be transformed into the starting compounds of this invention by solvolysis, hydrogenolysis and/or hydroxylation in the 12a position according to the methods described above.

If $R^5$ is a reactive radical (e.g., $NH_2$), it is sometimes advisable to protect this radical by a protecting group in a manner known per se.

The compounds of Formula I and their physiologically acceptable acid addition salts possess valuable pharmacological properties coupled with good toleration. For example, they exhibit a broad spectrum of antibacterial activity against both Gram-positive and Gram-negative bacteria, including tetracycline-resistant Gram-positive and tetracycline-resistant Gram-negative organisms.

Accordingly, the compounds of this invention can be used as medicines, especially as broad spectrum antibiotics for combating bacterial infections. They can also be used in intermediate products for the preparation of other medicines.

The novel compounds of Formula I and their physiologically acceptable acid addition salts can be used, mixed with solid, liquid and/or semi-liquid medicinal excipients, as medicaments in human and veterinary medicine. Examples of such excipients are organic or inorganic substances which are suitable for enteral or parenteral administration or topical application and which do not react with the new compounds, such as, for example, water, vegetable oils, polyethylene glycols, gelatin, lactose, starch, magnesium stearate, talc and white petroleum jelly. Tablets, dragees, capsules, syrups, elixirs or suppositories, for example, are suitable for enteral administration. Solutions, preferably oily or aqueous solutions, and suspensions, emulsions or implants, are in particular used for parenteral administration and ointments, creams or powders are used for topical application. These preparations can be sterilized and/or contain auxiliary agents, such as preservatives, stabilizers and/or wetting agents, salts for regulating osmotic pressure, buffer substances, dyestuffs, flavorings and/or scents. If desired, they can also contain one or more other active substances, for example, vitamins, e.g., vitamin $B_1$, $B_2$, $B_6$, $B_{12}$ and C.

As a rule, the novel compounds of this invention are administered analogously to the known tetracyclines, such as tetracycline, chlorotetracycline or hydroxytetracycline, preferably in doses of from about 10 to about 1,000, preferably from 50 to 500 mg. per dosage unit. The daily dose is preferably from 0.2 to 20 mg./kg. of body weight. Oral administration is preferred.

Each of the compounds of Formula I named in the examples which follow is particularly suitable for the production of pharmaceutical preparations.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

0.3 g of fluorosulfonic acid methyl ester is added to a solution of 560 mg of 4-de-dimethylamino-4-thiobenzamido-7-chloro-6-thiatetracycline (4-thiobenzamido-1,4,4a,5,5a,6,11,12a-octahydro-3,10,12,12a-tetrahydroxy-7-chloro-1,11-dioxo-6-thianaphthacene-2-carboxamide) and 850 mg of 1,8-bis-dimethylamino-naphthalene in a mixture of 50 ml of methylene chloride and 50 ml of methanol and the mixture is stirred under nitrogen for 25 minutes at 20°. The corresponding S-methyl-imino-thioether is formed. The mixture is then stirred into water and extracted with chloroform and the extracts are dried and evaporated. The residue is dissolved in THF, 1 N hydrochloric acid is added and the mixture is stirred for one hour at 20°. The THF is then distilled off and the residual aqueous solution, which contains hydrochloric acid, is extracted with butanol and the extract is evaporated. This gives 4-de-dimethylamino-4-amino-7-chloro-6-thiatetracycline (4-amino-1,4,4a,5,5a,6,11,12a-octahydro-3,10,12,12a-tetrahydroxy-7-chloro-1,11-dioxo-6-thianaphthacene-2-carboxamide) as the hydrochloride; m.p. above 270°.

The starting material can be obtained as follows:

a. A mixture of 450 ml of concentrated hydrochloric acid and 1,200 ml of water is added to 157.6 g of 2-chloro-5-methoxy-aniline, while stirring, and the mixture is diazotised with a solution of 69 g of $NaNO_2$ in 130 ml of water at 0°–5°. The mixture is then buffered with sodium acetate and the diazonium salt solution is added dropwise, while stirring, to a solution, at 70°, of 256 g of potassium ethylxanthate in 360 ml of water. After cooling, the mixture is worked up with $CH_2Cl_2$ and the resulting crude xanthic acid ester is saponified with KOH in ethanol and the mixture is evaporated, acidified and distilled with steam to give 2-chloro-5-methoxy-thiophenol; b.p. 110°/0.5 mm.

b. A mixture of 122 g of 2-chloro-5-methoxy-thiophenol and 10 ml of 10% sodium methylate solution is warmed to 80° and 123 g of glutaconic acid dimethyl ester are added dropwise, while stirring, at 80°. The mixture is then heated while stirring for a further hour at 80° and the product is poured into half-concentrated hydrochloric acid and the mixture boiled for 18 hours. On cooling 3-(2-chloro-5-methoxyphenyl-mercapto)-glutaric acid precipitates out; m.p. 133°–135°.

c. 17.5 g of this acid are allowed to stand with 70 g of hydrogen fluoride for 3 days at room temperature, the mixture is poured onto ice and filtered to give 5-methoxy-8-chloro-thiochroman-4-one-2-acetic acid; m.p. 169°–171°.

d. 28.7 g of the acid are suspended in 300 ml of chloroform and 23 g of $PCl_5$ are introduced at 5°–10°. The mixture is stirred for a further hour, the solvent is removed and the resulting crude acid chloride is dissolved in 50 ml of dioxane. The resulting solution is stirred slowly into 220 ml of 33% aqueous $NH_3$ solution to give 5-methoxy-8-chloro-thiochroman-4-one-2-acetamide; m.p. 198°–200°.

e. 32.5 g of p-toluenesulfonyl chloride are added to a suspension of 30.1 g of the amide in 450 ml of pyridine, while stirring, the mixture is stirred overnight, poured onto ice and worked up with chloroform and aqueous hydrochloric acid to give 5-methoxy-8-chloro-thiochroman-4-one-2-acetonitrile; m.p. 124°–126°.

f. A solution of 2.32 g of BBr$_3$ in 10 ml of methylene chloride is added dropwise, at −60° to −50°, to a solution of 2.28 g of the nitrile in 25 ml of methylene chloride and the mixture is allowed to come to 0° while continuing to stir. It is poured onto ice and worked up to give 5-hydroxy-8-chloro-thiochroman-4-one-2-acetonitrile; m.p. 140°–142°.

g. A solution of 28 g of Na$_3$PO$_4$ . 12 H$_2$O in 24 ml of water and 60 ml of acetic acid is added to a solution of 2.54 g of the nitrile in 24 ml of pyridine. 22 g of Raney nickel are now added, the mixture is stirred for 20 minutes under nitrogen, the catalyst is filtered off and the filtrate is worked up with dilute hydrochloric acid and chloroform. This gives 5-hydroxy-8-chloro-thiochroman-4-one-2-acetaldehyde; m.p. 90°–93°.

h. 7.7 g of the aldehyde are dissolved in 90 ml of absolute THF, 24 g of MgSO$_4$ and 10.8 g of Pb(OOCCH$_3$)$_2$ are added and a solution of 4.78 g of 2-phenyl-2-thiazolin-5-one in 30 ml of THF is then added dropwise, while stirring and passing in nitrogen, and the mixture is stirred for a further 5 minutes. The inorganic salts are filtered off, the filtrate is evaporated and the residue is treated with acetone, whereupon 2-phenyl-4-[2-(5-hydroxy-8-chloro-thiochroman-4-on-2-yl)-ethylidene]-2-thiazolin-5-one crystallises; m.p. 156°.

i. 8.3 g of the above thiazolinone and 3.5 g of acetone dicarboxylic acid monomethyl ester-monoamide are dissolved in a mixture of 100 ml of pyridine and 34 ml of DMF. 0.72 g of NaH are added while passing in nitrogen and the mixture is stirred for 2 hours while continuing to pass in nitrogen. A further 0.96 g of NaH is then added and the mixture is heated to the boil. After boiling for 20 minutes, a further 0.24 g of NaH is added and the mixture is boiled for a further 30 minutes. After cooling, methanol is added and the mixture is poured onto a mixture of hydrochloric acid and ice and worked up with chloroform. This gives an amorphous mixture of stereoisomeric 4-thiobenzamido-1,4,4a,5,5a,6,11,12a-octahydro-3,10,12-trihydroxy-7-chloro-1,11-dioxo-6-thianaphthacene-2-carboxamides. For epimerisation at C$_{(4)}$, the crude product is dissolved in 100 ml of pyridine and left to stand for 3 days at 20° while passing nitrogen through the solution. The solution is then stirred into a mixture of hydrochloric acid and ice water and extracted with chloroform. In order to separate the "natural" 6-thiatetracycline from the "unnatural" fraction, the residue obtained after distilling off the chloroform is chromatographed in chloroform on silica gel, 4-de-dimethylamino-4-thiobenzamido-7-chloro-12a-dehydroxy-6-thiatetracycline being obtained; m.p. 218°–220°.

j. 2 g of the above 6-thiatetracycline are dissolved in 100 ml of DMF, 240 ml of THF are added and 1.2 g of fine NaH are then added while stirring. While continuing to stir, oxygen is passed through the solution and, in the early part of this period, about 0.4 ml of water is sprayed in below the surface using a syringe. After 40 minutes the reaction mixture is stirred into dilute hydrochloric acid. The mixture is extracted with ethyl acetate, worked up and purified chromatographically on silica gel (elution agent chloroform) to give 4-de-dimethylamino-4-thiobenzamido-7-chloro-6-thiatetracycline; m.p. 222° (from acetone).

4-De-dimethylamino-4-amino-6-thiatetracycline,
4-de-dimethylamino-4-amino-7-fluoro-6-thiatetracycline,
4-de-dimethylamino-4-amino-8-fluoro-6-thiatetracycline,
4-de-dimethylamino-4-amino-9-fluoro-6-thiatetracycline,
4-de-dimethylamino-4-amino-8-chloro-6-thiatetracycline,
4-de-dimethylamino-4-amino-9-chloro-6-thiatetracycline,
4-de-dimethylamino-4-amino-7-bromo-6-thiatetracycline,
4-de-dimethylamino-4-amino-8-bromo-6-thiatetracycline,
4-de-dimethylamino-4-amino-9-bromo-6-thiatetracycline,
4-de-dimethylamino-4-amino-7-trifluoromethyl-6-thiatetracycline,
4-de-dimethylamino-4-amino-8-trifluoromethyl-6-thiatetracycline,
4-de-dimethylamino-4-amino-9-trifluoromethyl-6-thiatetracycline,
4-de-dimethylamino-4-amino-7-hydroxy-6-thiatetracycline,
4-de-dimethylamino-4-amino-8-hydroxy-6-thiatetracycline,
4-de-dimethylamino-4-amino-9-hydroxy-6-thiatetracycline,
4-de-dimethylamino-4-amino-7-methyl-6-thiatetracycline,
4-de-dimethylamino-4-amino-8-methyl-6-thiatetracycline,
4-de-dimethylamino-4-amino-9-methyl-6-thiatetracycline,
4-de-dimethylamino-4-amino-7-nitro-6-thiatetracycline,
4-de-dimethylamino-4-amino-8-nitro-6-thiatetracycline,
4-de-dimethylamino-4-amino-9-nitro-6-thiatetracycline,
4-de-dimethylamino-4,7-diamino-6-thiatetracycline,
4-de-dimethylamino-4,8-diamino-6-thiatetracycline,
4-de-dimethylamino-4,9-diamino-6-thiatetracycline,
4-de-dimethylamino-4-amino-7-methylamino-6-thiatetracycline,
4-de-dimethylamino-4-amino-8-methylamino-6-thiatetracycline,
4-de-dimethylamino-4-amino-9-methylamino-6-thiatetracycline,
4-de-dimethylamino-4-amino-7-dimethylamino-6-thiatetracycline,
4-de-dimethylamino-4-amino-8-dimethylamino-6-thiatetracycline and
4-de-dimethylamino-4-amino-9-dimethylamino-6-thiatetracycline are obtained analogously by splitting the corresponding 4-de-dimethylamino-4-thiobenzamido-6-thiatetracyclines.

EXAMPLE 2

Analogously to Example 1, 4-de-dimethylamino-4-amino-7-chloro-5a-epi-6-thiatetracycline (no. m.p. until 270°) is obtained from 4-de-dimethylamino-4-thiobenzamido-7-chloro-5a-epi-6-thiatetracycline (m.p. 215°) by reaction with fluorosulfonic acid methyl ester to give the corresponding S-methylimino-thioether and subsequent hydrolysis with hydrochloric acid.

The starting material can be obtained by isolating the corresponding 5a-epi-compound (m.p. 255°) when carrying out the chromatography in Example 1, paragraph i) and hydroxylating this compound in the 12a-position.

The corresponding 4-de-dimethylamino-4-amino-5a-epi-6-thiatetracyclines, for example 4-de-dimethylamino-4-amino-8-nitro-5a-epi-6-thiatetracycline  4-de-dimethylamino-4-amino-7-dimethylamino-5a-epi-6-thiatetracycline are obtained analogously by splitting the corresponding 4-de-dimethylamino-4-thiobenzamido-5a-epi-6-thiatetracyclines.

EXAMPLE 3

Analogously to Example 1, 4-de-dimethylamino-4-amino-8-methoxy-6-thiatetracycline (m.p. 235°–238°) is obtained from 4-de-dimethylamino-4-thiobenzamido-8-methoxy-6-thiatetracycline.

The starting material can be obtained as follows:

3,5-Dimethoxyphenol is reacted with N,N-dimethyl-thiocarbamoyl chloride in the presence of sodium hydride in DMF to give 1-dimethylaminothiocarbonyloxy-3,5-dimethoxybenzene of m.p. 77°–78°. This product is rearranged, by heating for half an hour at 270°, to give 1-dimethylaminocarbonylmercapto-3,5-dimethoxybenzene, which, in the crude state, by leaving to stand for 3 days with ethanolic KOH, is saponified to give 3,5-dimethoxythiophenol of b.p. 103°–109°/0.25 mm. Reaction with glutaconic acid dimethyl ester gives 3-(3,5-dimethoxyphenylmercapto)-glutaric acid dimethyl ester, which is converted, at 80° by means of polyphosphoric acid, into 5,7-dimethoxy-thiochroman-4-one-2-acetic acid methyl ester of m.p. 98°–99°. The corresponding free acid (m.p. 180°–182°) is converted, via the chloride and the amide (m.p. 199°–202°), into the corresponding nitrile (m.p. 123°–124°), which is split, by means of BBr$_3$, into 5-hydroxy-7-methoxy-thiochroman-4-one-2-acetonitrile (m.p. 97°–98°). Analogously to Example 1, there are obtained therefrom 5-hydroxy-7-methoxy-thiochroman-4-one-2-acetaldehyde (m.p. 112°–115°), 2-phenyl-4-[2-(5-hydroxy-7-methoxy-thiochroman-4-on-2-yl)-ethylidene]-2-thiazolin-5-one (m.p. 97°–99°), 4-thiobenzamido-1,4,4a,5,5a,6,11,12-octahydro-3,10,12-trihydroxy-8-methoxy-1,11-dioxo-6-thianaphthacene-2-carboxamide (mixture of stereo-isomers), 4-de-dimethylamino-4-thiobenzamido-8-methoxy-12a-dehydroxy-6-thiatetracycline (m.p. 212°–215°) and, finally, by hydroxylation 4-de-dimethylamino-4-thiobenzamido-8-methoxy-6-thiatetracycline (m.p. 168°–171°).
4-De-dimethylamino-4-amino-9-methoxy-6-thiatetracycline,
4-de-dimethylamino-4-amino-7-ethoxy-6-thiatetracycline,
4-de-dimethylamino-4-amino-8-ethoxy-6-thiatetracycline and
4-de-dimethylamino-4-amino-9-ethoxy-6-thiatetracycline, as well as the corresponding 5a-epi-compounds, for example, 4-de-dimethylamino-4-amino-8-methoxy-5a-epi-6-thiatetracycline, are obtained analogously.

EXAMPLE 4

Analogously to Example 1, 4-de-dimethylamino-4-amino-7-acetamido-6-thiatetracycline is obtained from 4-de-dimethylamino-4-thiobenzamido-7-acetamido-6-thiatetracycline.

The starting material can be obtained by reaction of 2-nitro-5-methoxyphenol with N,N-dimethyl-thiocarbamoyl chloride in DMF in the presence of NaH to give 1-dimethylamino-thiocarbonyloxy-2-nitro-5-methoxyphenol (m.p. 125°), rearrangement, by heating for half an hour at 210°, to give 1-dimethylaminocarbonylmercapto-2-nitro-5-methoxyphenol (m.p. 101°), saponification with aqueous-ethanolic sodium hydroxide solution at 20° to give 2-nitro-5-methoxy-thiophenol (m.p. 87°), addition reaction with glutaconic acid dimethyl ester to give 3-(2-nitro-5-methoxy-phenylmercapto)-glutaric acid dimethyl ester (m.p. 91°), saponification to give the free acid (m.p. 165°–166°), cyclization to give 5-methoxy-8-nitro-thiochroman-4-one-2-acetic acid (m.p. 182°–183°), conversion into the amide (m.p. 228°–230°), and the nitrile (m.p. 164°–165°), ether cleavage to yield 5-hydroxy-8-nitro-thiochroman-4-on-2-acetonitrile (m.p. 187°–188°), hydrogenation on 5% Pd-C in methanol at 20° and normal pressure to give 5-hydroxy-8-amino-thiochroman-4-one-2-acetonitrile (hydrochloride, m.p. 240° with decomposition), acetylation with ketene in dichloromethane/methanol to give 5-hydroxy-8-acetamidothiochroman-4-one-2-acetonitrile (m.p. 142°), reaction to give the aldehyde (m.p. 142°–144°) and condensation with 2-phenyl-2-thiazolin-5-one to give 2-phenyl-4-[2-(5-hydroxy-8-acetamidothiochroman-4-on-2-yl)-ethylidene]-2-thiazolin-5-one (m.p. 222°–224°), condensation with acetonedicarboxylic acid monomethyl ester-monoamide to give a mixture of stereoisomeric 4-thiobenzamido-1,4,4a,5,5a,6,11,12a-octahydro-3,10,12-trihydroxy-7-acetamido-1,11-dioxo-6-thianaphthacene-2-carboxamides (m.p. 238°–240° with decomposition), epimerization with pyridine at 40° to give a mixture (m.p. 228°–230° with decomposition) of 4-de-dimethylamino-4-thiobenzamido-7-acetamido-12a-de-hydroxy-6-thiatetracycline and its 5a-epimer, hydroxylation of the mixture and separation of the isomers via the imino ethers.

4-De-dimethylamino-4-amino-8-acetamido-6-thiatetracycline and 4-de-dimethylamino-4-amino-9-acetamido-6-thiatetracycline as well as the corresponding 5a-epi-compounds, for example, 4-de-dimethylamino-4-amino-7-acetamido-5a-epi-6-thiatetracycline, are obtained analogously.

EXAMPLE 5

Analogously to Example 1, 4-de-dimethylamino-4-amino-5-methyl-7-chloro-6-thiatetracycline is obtained from 4-de-dimethylamino-4-thiobenzamido-5-methyl-7-chloro-6-thiatetracycline.

The starting material can be obtained by condensation of 2-chloro-5-methoxythiophenol and 2-methylglutaconic acid dimethyl ester to give 2-methyl-3-(2-chloro-5-methoxyphenylmercapto)-glutaric acid, cyclization to give 2-(5-methoxy-8-chloro-thiochroman-4-on-2-yl)-propionic acid (a little 3-methyl-5-methoxy-8-chloro-thiochroman-4-one-2-acetic acid is also formed during the cyclization and is separated off chromatographically), successive conversion into the acid chloride, the amide and the nitrile and ether splitting to give 2-(5-hydroxy-8-chloro-thiochroman-4-on-2-yl)-propionitrile, reaction to give the aldehyde and condensation with 2-phenyl-2-thiazolin-5-one to give 2-phenyl-4-[2-(5-hydroxy-8-chloro-thiochroman-4-on-2-yl)-propylidene]-2-thiazolin-5-one, condensation with acetonedicarboxylic acid monomethyl ester-monoamide to give a mixture of stereoisomeric 4-thiobenzamido-1,4,4a,5,5a,6,11,12a-octahydro-3,10,12-trihydroxy-7-chloro-5-methyl-1,11-dioxo-6-thianaphthacene-2-carboxamides, epimerization with pyridine to give 4-de-dimethylamino-4-thiobenzamido-5-methyl-7-chloro-12a-dehydroxy-6-thiatetracycline and hydroxylation.

4-De-dimethylamino-4-amino-5-ethyl-7-chloro-6-thiatetracycline,
4-de-dimethylamino-4-amino-5-n-propyl-7-chloro-6-thiatetracycline,
4-de-dimethylamino-4-amino-5-n-butyl-7-chloro-6-thiatetracycline,
4-de-dimethylamino-4-amino-5,5-dimethyl-7-chloro-6-thiatetracycline,
4-de-dimethylamino-4-amino-5-methyl-5-ethyl-7-chloro-6-thiatetracycline and
4-de-dimethylamino-4-amino-5,5-diethyl-7-chloro-6-thiatetracycline, as well as the corresponding 5a-epi-compounds, can be obtained analogously from the corresponding starting materials which are alkylated in the 5-position.

EXAMPLE 6

Analogously to Example 1, 4-de-dimethylamino-4-amino-6-methyl-6-aza-tetracycline is obtained from 4-de-dimethylamino-4-thiobenzamido-6-methyl-6-aza-tetracycline (4-thiobenzamido-1,4,4a,5,5a,6,11,12a-octahydro-3,10,12,12a-tetrahydroxy-6-methyl-1,11-dioxo-6-aza-naphthacene-2-carboxamide).

The starting material can be obtained by condensation of 3-amino-4-chloroanisole with acetonedicarboxylic acid dimethyl ester to give 4-oxo-5-methoxy-8-chloro-1,4-dihydro-quinoline-2-acetic acid methyl ester, hydrogenation on 5% Pd-on-charcoal in dioxan at 6 atmospheres and 60° to give 4-oxo-5-methoxy-1,4-dihydroquinoline-2-acetic acid methyl ester, reaction with dimethyl sulphate in sodium hydroxide solution to give 1-methyl-4-oxo-5-methoxy-1,4-dihydroquinoline-2-acetic acid, hydrogenation on PtO$_2$ in methanol at 20° and normal pressure to give 1-methyl-4-oxo-5-methoxy-1,2,3,4-tetrahydroquinoline-2-acetic acid, reaction, via the chloride and the amide, to give the nitrile, ether splitting by means of BBr$_3$ to give 1-methyl-4-oxo-5-hydroxy-1,2,3,4-tetrahydroquinoline-2-acetonitrile, reaction with Raney nickel to give 1-methyl-4-oxo-5-hydroxy-1,2,3,4-tetrahydroquinoline-2-acetaldehyde, condensation with 2-phenyl-2-thiazolin-5-one to give 2-phenyl-4-[2-(1-methyl-4-oxo-5-hydroxy-1,2,3,4-tetrahydro-2-quinolyl)-ethylidene]-2-thiazolin-5-one, condensation with acetone dicarboxylic acid monomethyl ester-monoamide to give 4-thiobenzamido-1,4,4a,5,5a,6,11,12-octahydro-3,10,12-trihydroxy-6-methyl-1,11-dioxo-6-aza-naphthacene-2-carboxamide (mixture of stereoisomers), epimerization with pyridine to give 4-de-dimethylamino-4-thiobenzamido-6-methyl-12a-dehydroxy-6-aza-tetracycline and hydroxylation.

4-De-dimethylamino-4-amino-6-methyl-7-fluoro-6-azatetracycline,
4-de-dimethylamino-4-amino-6-methyl-8-fluoro-6-azatetracycline,
4-de-dimethylamino-4-amino-6-methyl-9-fluoro-6-azatetracycline,
4-de-dimethylamino-4-amino-6-methyl-7-chloro-6-azatetracycline,
4-de-dimethylamino-4-amino-6-methyl-8-chloro-6-azatetracycline,
4-de-dimethylamino-4-amino-6-methyl-9-chloro-6-azatetracycline,
4-de-dimethylamino-4-amino-6-methyl-7-bromo-6-azatetracycline,
4-de-dimethylamino-4-amino-6-methyl-8-bromo-6-azatetracycline,
4-de-dimethylamino-4-amino-6-methyl-9-bromo-6-azatetracycline,
4-de-dimethylamino-4-amino-6-methyl-7-trifluoromethyl-6-azatetracycline,
4-de-dimethylamino-4-amino-6-methyl-8-trifluoromethyl-6-azatetracycline,
4-de-dimethylamino-4-amino-6-methyl-9-trifluoromethyl-6-azatetracycline,
4-de-dimethylamino-4-amino-6-methyl-7-hydroxy-6-azatetracycline,
4-de-dimethylamino-4-amino-6-methyl-8-hydroxy-6-azatetracycline,
4-de-dimethylamino-4-amino-6-methyl-9-hydroxy-6-azatetracycline,
4-de-dimethylamino-4-amino-6,7-dimethyl-6-azatetracycline,
4-de-dimethylamino-4-amino-6,8-dimethyl-6-azatetracycline, 4-de-dimethylamino-4-amino-6,9-dimethyl-6-azatetracycline,
4-de-dimethylamino-4-amino-6-methyl-7-methoxy-6-azatetracycline,
4-de-dimethylamino-4-amino-6-methyl-8-methoxy-6-azatetracycline,
4-de-dimethylamino-4-amino-6-methyl-9-methoxy-6-azatetracycline,
4-de-dimethylamino-4-amino-6-methyl-7-ethoxy-6-azatetracycline,
4-de-dimethylamino-4-amino-6-methyl-8-ethoxy-6-azatetracycline,
4-de-dimethylamino-4-amino-6-methyl-9-ethoxy-6-azatetracycline,
4-de-dimethylamino-4-amino-6-methyl-7-nitro-6-azatetracycline,
4-de-dimethylamino-4-amino-6-methyl-8-nitro-6-azatetracycline,
4-de-dimethylamino-4-amino-6-methyl-9-nitro-6-azatetracycline,
4-de-dimethylamino-4,7-diamino-6-methyl-6-azatetracycline,
4-de-dimethylamino-4,8-diamino-6-methyl-6-azatetracycline,
4-de-dimethylamino-4,9-diamino-6-methyl-6-azatetracycline,
4-de-dimethylamino-4-amino-6-methyl-7-methylamino-6-azatetracycline,
4-de-dimethylamino-4-amino-6-methyl-8-methylamino-6-azatetracycline, 4-de-dimethylamino-4-amino-6-methyl-9-methylamino-6-azatetracycline,
4-de-dimethylamino-4-amino-6-methyl-7-dimethylamino-6-azatetracycline,
4-de-dimethylamino-4-amino-6-methyl-8-dimethylamino-6-azatetracycline,
4-de-dimethylamino-4-amino-6-methyl-9-dimethylamino-6-azatetracycline,
4-de-dimethylamino-4-amino-6-methyl-7-acetamido-6-azatetracycline,
4-de-dimethylamino-4-amino-6-methyl-8-acetamido-6-azatetracycline and
4-de-dimethylamino-4-amino-6-methyl-9-acetamido-6-azatetracycline as well as the corresponding 5a-epi-compounds, for example, 4-de-dimethylamino-4-amino-6-methyl-5a-epi-6-azatetracycline, are obtained analogously.

EXAMPLE 7

Analogously to Example 1, 4-de-dimethylamino-4-amino-6-acetyl-6-azatetracycline is obtained from 4-de-dimethylamino-4-thiobenzamido-6-acetyl-6-azatetracycline (4-thiobenzamido-1,4,4a,5,5a,6,11,12a-octahydro-3,10,12,12a-tetrahydroxy-6-acetyl-1,11-dioxo-6-aza-naphthacene-2-carboxamide).

The starting material can be obtained by hydrogenation of 4-oxo-5-methoxy-1,4-dihydro-quinoline-2-acetic acid methyl ester to give 4-oxo-5-methoxy-1,2,3,4-tetrahydroquinoline-2-acetic acid methyl ester, saponification to give the free acid, acetylation to give 1-acetyl-4-oxo-5-methoxy-1,2,3,4-tetrahydro-quinoline-2-acetic acid, ether splitting by means of HBr/acetic acid, reaction into the chloride, Rosenmund reduction to give 1-acetyl-4-oxo-5-hydroxy-1,2,3,4-tetrahydro-quinoline-2-acetaldehyde, condensation with 2-phenyl-2-thiazolin-5-one to give 2-phenyl-4-[2-(1-acetyl-4-oxo-5-hydroxy-1,2,3,4-tetrahydro-2-quinolyl)-ethylidene]-2-thiazolin-5-one, condensation with acetonedicarboxylic acid monomethyl ester-monoamide to give 4-thiobenzamido-1,4,4a,5,,5a,6,11,12-octahydro-3,10,12-trihydroxy-6-acetyl-1,11-dioxo-6-aza-naphthacene-2-carboxamide (mixture of stereoisomers), epimerization with pyridine to give 4-de-dimethylamino-4-thiobenzamido-6-acetyl-12a-de-hydroxy-6-aza-tetracycline and hydroxylation.

4-De-dimethylamino-4-amino-6-acetyl-7-fluoro-6-azatetracycline,
4-de-dimethylamino-4-amino-6-acetyl-8-fluoro-6-azatetra-cycline,
4-de-dimethylamino-4-amino-6-acetyl-9-fluoro-6-azatetracycline,
4-de-dimethylamino-4-amino-6-acetyl-7-chloro-6-azatetracycline,
4-de-dimethylamino-4-amino-6-acetyl-8-chloro-6-azatetracycline,
4-de-dimethylamino-4-amino-6-acetyl-9-chloro-6-azatetracycline,
4-de-dimethylamino-4-amino-6-acetyl-7-bromo-6-azatetracycline,
4-de-dimethylamino-4-amino-6-acetyl-8-bromo-6-azatetracycline,
4-de-dimethylamino-4-amino-6-acetyl-9-bromo-6-azatetracycline,
4-de-dimethylamino-4-amino-6-acetyl-7-trifluoromethyl-6-azatetracycline,
4-de-dimethylamino-4-amino-6-acetyl-8-trifluoromethyl-6-azatetracycline,
4-de-dimethylamino-4-amino-6-acetyl-9-trifluoromethyl-6-azatetracycline,
4-de-dimethylamino-4-amino-6-acetyl-7-hydroxy-6-azatetracycline,
4-de-dimethylamino-4-amino-6-acetyl-8-hydroxy-6-azatetracycline,
4-de-dimethylamino-4-amino-6-acetyl-9-hydroxy-6-azatetracycline,
4-de-dimethylamino-4-amino-6-acetyl-7-methyl-6-azatetracycline,
4-de-dimethylamino-4-amino-6-acetyl-8-methyl-6-azatetracycline,
4-de-dimethylamino-4-amino-6-acetyl-9-methyl-6-azatetracycline,
4-de-dimethylamino-4-amino-6-acetyl-7-methoxy-6-azatetracycline,
4-de-dimethylamino-4-amino-6-acetyl-8-methoxy-6-azatetracycline,
4-de-dimethylamino-4-amino-6-acetyl-9-methoxy-6-azatetracycline,
4-de-dimethylamino-4-amino-6-acetyl-7-ethoxy-6-azatetracycline,
4-de-dimethylamino-4-amino-6-acetyl-9-ethoxy-6-azatetracycline,
4-de-dimethylamino-4-amino-6-acetyl-9-ethoxy-6-azatetracycline,
4-de-dimethylamino-4-amino-6-acetyl-7-nitro-6-azatetracycline,
4-de-dimethylamino-4-amino-6-acetyl-8-nitro-6-azatetracycline,
4-de-dimethylamino-4-amino-6-acetyl-9-nitro-6-azatetracycline,
4-de-dimethylamino-4,7-diamino-6-acetyl-6-azatetracycline,
4-de-dimethylamino-4,8-diamino-6-acetyl-6-azatetracycline,
4-de-dimethylamino-4,9-diamino-6-acetyl-6-azatetracycline,
4-de-dimethylamino-4-amino-6-acetyl-7-methylamino-6-azatetracycline,
4-de-dimethylamino-4-amino-6-acetyl-8-methylamino-6-azatetracycline,
4-de-dimethylamino-4-amino-6-acetyl-9-methylamino-6-azatetracycline,
4-de-dimethylamino-4-amino-6-acetyl-7-dimethylamino-6-azatetracycline,
4-de-dimethylamino-4-amino-6-acetyl-8-dimethylamino-6-azatetracycline,
4-de-dimethylamino-4-amino-6-acetyl-9-dimethylamino-6-azatetracycline,
4-de-dimethylamino-4-amino-6-acetyl-7-acetamido-6-azatetracycline,
4-de-dimethylamino-4-amino-6-acetyl-8-acetamido-6-azatetracycline and
4-de-dimethylamino-4-amino-6-acetyl-9-acetamido-6-azatetracycline, as well as the corresponding 5a-epi-compounds, for example, 4-de-dimethylamino-4-amino-6-acetyl-5a-epi-6-azatetracycline, are obtained analogously.

EXAMPLE 8

550 mg of 4-de-dimethylamino-4-benzamido-5,5-dimethyl-8-methoxy-6-oxatetracycline (4-benzamido-1,4,4a,5,5a,6,11,12a-octahydro-3,10,12,12a-tetrahydroxy-8-methoxy-5,5-dimethyl-1,11-dioxo-6-oxanaphthacene-2-carboxamide) are heated with 15 ml of acetic acid and 10 ml of 48% hydrobromic acid at 90° for 6 hours, the mixture is poured onto ice, washed with chloroform and extracted with n-butanol. After filtration through silica gel, 4-de-dimethylamino-4-amino-5,5-dimethyl-8-methoxy-6-oxatetracycline is obtained.

The starting material can be obtained as follows:

a. 120 g of 2,4,6-trihydroxyacetophenone are suspended in 5.5 l of chloroform, 730 ml of N,N-diisopropyl-ethylamine and 334 ml of dimethyl sulfate are added and the mixture is stirred for 24 hours at 20° and worked up to give 2-hydroxy-4,6-dimethoxyacetophenone; m.p. 74°–76°.

b. A mixture of 73.5 g of 2-hydroxy-4,6-dimethoxyacetophenone, 260 g of dimethylcyanoacetic acid ethyl ester and 375 ml of absolute dioxane is introduced into a suspension of 28.6 g of NaH in 7.3 g of dimethylcyanoacetic acid ethyl ester at 0°–10°, while stirring. The mixture is heated for 1 hour at 80°, cooled and poured into acetic acid and the resulting solution is stirred into ice water to give 2,2-dimethyl-3,5-dioxo-5-(2-hydroxy-4,6-dimethoxyphenyl)-pentanonitrile; m.p. 112°–113°.

c. 72 g of the above nitrile are heated with 430 ml of concentrated sulphuric acid at 90° to 100° for 1 hour and the mixture is poured onto ice to give 2-(1-carbamoyl-1-methylethyl)-5,7-dimethoxychromone; m.p. 217°–219°.

d. Hydrogenation of the above compound over PdO on BaSO₄ (2.5%) in ethanol at 20° and normal pressure gives 2-(1-carbamoyl-1-methylethyl)-5,7-dimethoxy-4-chromanone; m.p. 161°–163°.

e. 24 g of the above keto-amide with 42.5 g of p-toluenesulphochloride are stirred in 600 ml of pyridine, under nitrogen, for 16 hours at 20° and the mixture is poured onto ice to give 2-(1-cyano-1-methylethyl)-5,7-dimethoxy-4-chromanone; m.p. 170°.

f. Reaction of the above ketonitrile with BBr₃ in methylene chloride at −50° to −40° gives 2-(1-cyano-1-methylethyl)-5-hydroxy-7-methoxy-4-chromanone; m.p. 130°.

g. Reaction of the above nitrile with Raney nickel gives 2-(1-formyl-1-methylethyl)-5-hydroxy-7-methoxy-4-chromanone; m.p. 93°–94°.

h. Reaction of the aldehyde with 2-phenyl-2-oxazolin-5-one gives 2-phenyl-4-[2-methyl-2-(5-hydroxy-7-methoxychroman-4-on-2-yl)-propylidene]-2-oxazolin-5-one; m.p. 147°–149°.

i. Reaction of the above oxazolinone with acetonedicarboxylic acid monomethyl ester-monoamide gives a mixture of stereoisomeric 4-benzamido-1,4,4a,5,5a,6,11,12a-octahydro-3,10,12-trihydroxy-8-methoxy-5,5-dimethyl-1,11-dioxo-6-oxanaphthacene-2-carboxamides; m.p. 271°–274°.

j. C₍₄₎-Epimerization of the above mixture with pyridine gives a mixture of 4-de-dimethylamino-4-benzamido-5,5-dimethyl-8-methoxy-12a-dehydroxy-6-oxatetracycline and its 5a-epimer, which is separated chromatographically on silica gel.

k. 12a-Hydroxylation of 4-de-dimethylamino-4-benzamido-5,5-dimethyl-8-methoxy-12a-dehydroxy-6-oxatetracycline in the presence of NaH in DMF/THF gives 4-de-dimethylamino-4-benzamido-5,5-dimethyl-8-methoxy-6-oxatetracycline.

4-De-dimethylamino-4-amino-6-oxatetracycline,
4-de-dimethylamino-4-amino-7-fluoro-6-oxatetracycline,
4-de-dimethylamino-4-amino-8-fluoro-6-oxatetracycline,
4-de-dimethylamino-4-amino-9-fluoro-6-oxatetracycline,
4-de-dimethylamino-4-amino-7-chloro-6-oxatetracycline,
4-de-dimethylamino-4-amino-8-chloro-6-oxatetracycline,
4-de-dimethylamino-4-amino-9-chloro-6-oxatetracycline,
4-de-dimethylamino-4-amino-7-bromo-6-oxatetracycline,
4-de-dimethylamino-4-amino-8-bromo-6-oxatetracycline,
4-de-dimethylamino-4-amino-9-bromo-6-oxatetracycline,
4-de-dimethylamino-4-amino-7-trifluoromethyl-6-oxatetracycline,
4-de-dimethylamino-4-amino-8-trifluoromethyl-6-oxatetracycline,
4-de-dimethylamino-4-amino-9-trifluoromethyl-6-oxatetracycline,
4-de-dimethylamino-4-amino-7-hydroxy-6-oxatetracycline,
4-de-dimethylamino-4-amino-8-hydroxy-6-oxatetracycline,
4-de-dimethylamino-4-amino-9-hydroxy-6-oxatetracycline,
4-de-dimethylamino-4-amino-7-methyl-6-oxatetracycline,
4-de-dimethylamino-4-amino-8-methyl-6-oxatetracycline,
4-de-dimethylamino-4-amino-9-methyl-6-oxatetracycline,
4-de-dimethylamino-4-amino-7-methoxy-6-oxatetracycline,
4-de-dimethylamino-4-amino-8-methoxy-6-oxatetracycline,
4-de-dimethylamino-4-amino-9-methoxy-6-oxatetracycline,
4-de-dimethylamino-4-amino-7-ethoxy-6-oxatetracycline,
4-de-dimethylamino-4-amino-8-ethoxy-6-oxatetracycline,
4-de-dimethylamino-4-amino-9-ethoxy-6-oxatetracycline,
4-de-dimethylamino-4-amino-7-nitro-6-oxatetracycline,
4-de-dimethylamino-4-amino-8-nitro-6-oxatetracycline,
4-de-dimethylamino-4-amino-9-nitro-6-oxatetracycline,
4-de-dimethylamino-4,7-diamino-6-oxatetracycline,
4-de-dimethylamino-4,8-diamino-6-oxatetracycline,
4-de-dimethylamino-4,9-diamino-6-oxatetracycline,
4-de-dimethylamino-4-amino-7-methylamino-6-oxatetracycline,
4-de-dimethylamino-4-amino-8-methylamino-6-oxatetracycline,
4-de-dimethylamino-4-amino-9-methylamino-6-oxatetracycline, 4-de-dimethylamino-4-amino-7-dimethylamino-6-oxatetracycline,
4-de-dimethylamino-4-amino-8-dimethylamino-6-oxatetracycline,
4-de-dimethylamino-4-amino-9-dimethylamino-6-oxatetracycline,
4-de-dimethylamino-4-amino-7-acetamido-6-oxatetracycline,
4-de-dimethylamino-4-amino-8-acetamido-6-oxatetracycline,
4-de-dimethylamino-4-amino-9-acetamido-6-oxatetracycline,
4-de-dimethylamino-4-amino-5,5-dimethyl-6-oxatetracycline,
4-de-dimethylamino-4-amino-5,5-dimethyl-7-fluoro-6-oxatetracycline,
4-de-dimethylamino-4-amino-5,5-dimethyl-8-fluoro-6-oxatetracycline,
4-de-dimethylamino-4-amino-5,5-dimethyl-9-fluoro-6-oxatetracycline,
4-de-dimethylamino-4-amino-5,5-dimethyl-7-chloro-6-oxatetracycline,
4-de-dimethylamino-4-amino-5,5-dimethyl-8-chloro-6-oxatetracycline,
4-de-dimethylamino-4-amino-5,5-dimethyl-9-chloro-6-oxatetracycline,
4-de-dimethylamino-4-amino-5,5-dimethyl-7-bromo-6-oxatetracycline,
4-de-dimethylamino-4-amino-5,5-dimethyl-8-bromo-6-oxatetracycline,
4-de-dimethylamino-4-amino-5,5-dimethyl-9-bromo-6-oxatetracycline,
4-de-dimethylamino-4-amino-5,5-dimethyl-7-trifluoromethyl-6-oxatetracycline,
4-de-dimethylamino-4-amino-5,5-dimethyl-8-trifluoromethyl-6-oxatetracycline,
4-de-dimethylamino-4-amino-5,5-dimethyl-9-trifluoromethyl-6-oxatetracycline,
4-de-dimethylamino-4-amino-5,5-dimethyl-7-hydroxy-6-oxatetracycline,
4-de-dimethylamino-4-amino-5,5-dimethyl-8-hydroxy-6-oxatetracycline,
4-de-dimethylamino-4-amino-5,5-dimethyl-9-hydroxy-6-oxatetracycline,
4-de-dimethylamino-4-amino-5,5,7-trimethyl-6-oxatetracycline,
4-de-dimethylamino-4-amino-5,5,8-trimethyl-6-oxatetracycline,
4-de-dimethylamino-4-amino-5,5,9-trimethyl-6-oxatetracycline,
4-de-dimethylamino-4-amino-5,5-dimethyl-7-methoxy-6-oxatetracycline,
4-de-dimethylamino-4-amino-5,5-dimethyl-9-methoxy-6-oxatetracycline,
4-de-dimethylamino-4-amino-5,5-dimethyl-7-ethoxy-6-oxatetracycline,
4-de-dimethylamino-4-amino-5,5-dimethyl-8-ethoxy-6-oxatetracycline,
4-de-dimethylamino-4-amino-5,5-dimethyl-9-ethoxy-6-oxatetracycline,
4-de-dimethylamino-4-amino-5,5-dimethyl-7-nitro-6-oxatetracycline,
4-de-dimethylamino-4-amino-5,5-dimethyl-8-nitro-6-oxatetracycline,
4-de-dimethylamino-4-amino-5,5-dimethyl-9-nitro-6-oxatetracycline,
4-de-dimethylamino-4,7-diamino-5,5-dimethyl-6-oxatetracycline,
4-de-dimethylamino-4,8-diamino-5,5-dimethyl-6-oxatetracycline,
4-de-dimethylamino-4,9-diamino-5,5-dimethyl-6-oxatetracycline,
4-de-dimethylamino-4-amino-5,5-dimethyl-7-methylamino-6-oxatetracycline,
4-de-dimethylamino-4-amino-5,5-dimethyl-8-methylamino-6-oxatetracycline,
4-de-dimethylamino-4-amino-5,5-dimethyl-9-methylamino-6-oxatetracycline,
4-de-dimethylamino-4-amino-5,5-dimethyl-7-dimethylamino-6-oxatetracycline,
4-de-dimethylamino-4-amino-5,5-dimethyl-8-dimethylamino-6-oxatetracycline,
4-de-dimethylamino-4-amino-5,5-dimethyl-9-dimethylamino-6-oxatetracycline,
4-de-dimethylamino-4-amino-5,5-dimethyl-7-acetamido-6-oxatetracycline,
4-de-dimethylamino-4-amino-5,5-dimethyl-8-acetamido-6-oxatetracycline, and
4-de-dimethylamino-4-amino-5,5-dimethyl-9-acetamido-6-oxatetracycline, as well as the corresponding 5a-epi-compounds, for example, 4-de-dimethylamino-4-amino-5,5-dimethyl-8-methoxy-5a-epi-6-oxatetracycline, are obtained analogously.

EXAMPLE 9

552 mg of 4-de-dimethylamino-4-benzamido-8-methoxy-10-0-methyl-6-thiatetracycline [m.p. 194°–200°; obtainable from 5,7-dimethoxy-thiochroman-4-one-2-acetonitrile (compare Example 3) via 5,7-dimethoxy-thiochroman-4-one-2-acetaldehyde (m.p. 70°–72°), 2-phenyl-4-[2-(5,7-dimethoxy-thiochroman-4-on-2-yl)-ethylidene]-2-oxazolin-5-one (m.p. 87°–91°), 4-benzamido-1,4,4a,5,5a,6,11,12-octahydro-3,12-dihydroxy-8,10-dimethoxy-1,11-dioxo-6-thianaphthacene-2-carboxamide (mixture of stereoisomers; m.p. 217°–220°) and 4-de-dimethylamino-4-benzamido-8-methoxy-10-0-methyl-12a-dehydroxy-6-thiatetracycline] are heated with 2 ml of 48% hydrobromic acid and 3 ml of acetic acid for 4 hours at 90° and the mixture is worked up analogously to Example 8 to give 4-de-dimethylamino-4-amino-8-methoxy-6-thiatetracycline.

4-De-dimethylamino-4-amino-7-chloro-6-thiatetracycline-6,6-dioxide is obtained analogously from 4-de-dimethylamino-4-benzamido-7-chloro-10-0-methyl-6-thiatetracycline-6,6-dioxide [obtainable by oxidation of 5-methoxy-8-chloro-thiochroman-4-one-2-acetamide with $H_2O_2$ to give the corresponding sulphone (m.p. 192°–193°) and further via 5-methoxy-8-chloro-thiochroman-4-one-2-acetonitrile-1,1-dioxide, 5-methoxy-8-chloro-thiochroman-4-one-2-acetaldehyde-1,1-dioxide (m.p. 122°–124°) and 2-phenyl-4-[2-(5-methoxy-8-chloro-thiochroman-4-one-1,1-dioxid-2-yl)-ethylidene]-2-oxazolin-5-one (m.p. 185°)].

EXAMPLE 10

20 ml of 6 N hydrochloric acid are added to a solution of 467 mg of 4-de-dimethylamino-4-formamido-7-chloro-6-thiatetracycline (obtainable from 4-de-dimethylamino-4-thiobenzamido-7-chloro-12a-dehydroxy-6-thiatetracycline by solvolysis to give the 4-amino compound, formylation to give 4-de-dimethylamino-4-formamido-7-chloro-12a-dehydroxy-6-thiatetracycline and oxidation with $O_2$/NaH) in 20 ml of dioxane and the mixture is heated at 50° for 2 hours, diluted with water and extracted with butanol. The extract is dried and evaporated to give 4-de-dimethylamino-4-amino-7-chloro-6-thiatetracycline hydrochloride; m.p. above 270°.

EXAMPLE 11

481 mg of 7-chloro-10-0-methyl-6-thiatetracycline (4-dimethylamino-1,4,4a,5,5a,6,11,12a-octahydro-3,12,12a-trihydroxy-7-chloro-10-methoxy-1,11-dioxo-6-thia-naphthacene-2-carboxamide) are heated with 5 ml of a 40% solution of HBr in acetic acid at 100° for 15 minutes, the mixture is poured into water and extracted with n-butanol and after the customary working up 7-chloro-6-thiatetracycline (4-dimethylamino-1,4,4a,5,5a,6,11,12a-octahydro-3,10,12,12a-tetrahydroxy-7-chloro-1,11-dioxo-6-thianaphthacene-2-carboxamide) is obtained; m.p. 223°.

The starting material can be prepared from 5-methoxy-8-chloro-thiochroman-4-one-2-acetonitrile via 5-methoxy-8-chloro-thiochroman-4-one-2-acetaldehyde, 2-phenyl-4-[2-(5-methoxy-8-chloro-thiochroman-4-on-2-yl)-ethylidene]-2-thiazolin-5-one (m.p. 164°–166°), 4-thiobenzamido-1,4,4a,5,5a,6,11,12a-octahydro-3,12-dihydroxy-7-chloro-10-methoxy-1,11-dioxo-6-thia-naphthacene-2-carboxamide (mixture from which 2 epimers of m.p. 244°–246° and 206°, respectively, can be isolated chromatographically), 4-de-dimethylamino-4-thiobenzamido-7-chloro-10-0-methyl-12a-dehydroxy-6-thia-tetracycline (m.p. 252°, from the high-melting epimer by means of pyridine), 4-de-dimethylamino-4-thiobenzamido-7-chloro-10-0-methyl-6-thiatetracycline and 4-de-dimethylamino-4-amino-7-chloro-10-0-methyl-6-thiatetracycline.

EXAMPLE 12

Analogously to Example 11, 5,5-dimethyl-8-methoxy-6-oxa-tetracycline is obtained from 5,5-dimethyl-8-methoxy-10-0-methyl-6-oxatetracycline (4-dimethylamino-1,4,4a,5,5a,6,11,12a-octahydro-3,12,12a-trihydroxy-8,10-dimethoxy-1,11-dioxo-6-oxa-naphthacene-2-carboxamide) by means of HBr in acetic acid.

The starting material can be obtained by reaction of 2-(1-cyano-1-methylethyl)-5,7-dimethoxy-4-chromanone with Raney nickel to give 2-(1-formyl-1-methylethyl)-5,7-dimethoxy-4-chromanone (m.p. 97°–98°), reaction with 2-phenyl-2-thiazolin-5-one to give 2-phenyl-4-[2-methyl-2-(5,7-dimethoxy-chroman-4-on-2-yl)-propylidene]-2-thiazolin-5-one (m.p. 159°–160°), reaction of the thiazolinon with acetonedicarboxylic acid monomethyl ester-monoamide to give a mixture of 4-thiobenzamido-1,4,4a,5,5a,6,11,12a-octahydro-3,12-dihydroxy-8,10-dimethoxy-1,11-dioxo-6-oxa-naphthacene-2-carboxamides, epimerization with pyridine and chromatographic separation, hydroxylation of the resulting 4-de-dimethylamino-4-thiobenzamido-5,5-dimethyl-8-methoxy-10-0-methyl-12a-dehydroxy-6-oxatetracycline to give 4-de-dimethylamino-4-thiobenzamido-5,5-dimethyl-8-methoxy-10-0-methyl-6-oxatetracycline, splitting off the thiobenzoyl group analogously to Example 1, 4-de-dimethylamino-4-amino-5,5-dimethyl-8-methoxy-10-0-methyl-6-oxatetracycline (hydrobromide, m.p. above 300°) being formed, and methylation analogously to Example 18.

EXAMPLE 13

0.5 g of triethyloxonium tetrafluoborate is added to a solution of 538 mg of 4-de-dimethylamino-4-benzamido-8-methoxy-6-thiatetracycline [obtainable from 5-hydroxy-7-methoxy-thiochroman-4-one-2-acetaldehyde via 2-phenyl-4-[2-(5-hydroxy-7-methoxy-thiochroman-4-on-2-yl)-ethylidene]-2-oxazolin-5-one, 4-benzamido-1,4,4a,5,5a,6,11,12a-octahydro-3,10,12-trihydroxy-8-methoxy-1,11-dioxo-6-thianaphthacene-2-carboxamide (mixture of stereoisomers) and 4-de-dimethylamino-4-benzamido-8-methoxy-12a-dehydroxy-6-thiatetracycline (m.p. 235°–239°)] and 850 mg of 1,8-bis-dimethylamino-naphthalene in 100 ml of THF and the mixture is stirred under nitrogen for 48 hours at 20°. The 0-ethyliminoether formed is hydrolysed analogously to Example 1. This gives 4-de-dimethylamino-4-amino-8-methoxy-6-thiatetracycline.

4-De-dimethylamino-4-amino-7-chloro-6-thiatetracycline hydrochloride of m.p. above 270° is obtained analogously from 4-de-dimethylamino-4-benzamido-7-chloro-6-thiatetracycline [obtainable from 5-methoxy-8-chloro-thiochroman-4-one-2-acetaldehyde via 2-phenyl-4-[2-(5-methoxy-8-chloro-thiochroman-4-on-2-yl)-ethylidene]-2-oxazolin-5-one (m.p. 169°–170°)].

EXAMPLE 14

A solution of 100 mg of 7-chloro-10-0-benzyl-6-thiatetracycline (10-benzyloxy-4-dimethylamino-1,4,4a,5,5a,6,11,12a-octahydro-3,12,12a-trihydroxy-7-chloro-1,11-dioxo-6-thianaphthacene-2-carboxamide) in 25 ml of methanol is hydrogenated, at 20° and 1 atmosphere, on 50 mg of 5% Pd-on-charcoal until the absorption of $H_2$ has ceased. The mixture is filtered and the filtrate is evaporated to give 7-chloro-6-thiatetracycline; m.p. 223°.

5,5-Dimethyl-8-hydroxy-6-oxatetracycline is obtained analogously from 5,5-dimethyl-8-benzyloxy-10-0-benzyl-6-oxatetracycline [obtainable by reaction of 2-(1-carbamoyl-1-methylethyl)-5,7-dimethoxy-4-chromanone with HBr/acetic acid to give 2-(1-carbamoyl-1-methylethyl)-5,7-dihydroxy-4-chromanone, benzylation, conversion into the nitrile, reaction with Raney nickel to give 2-(1-formyl-1-methylethyl)-5,7-dibenzyloxy-4-chromanone, condensation with 2-phenyl-2-thiazolin-5-one to give 2-phenyl-4-[2-methyl-2-(5,7-dibenzyloxy-chroman-4-on-2-yl)-propylidene]-2-thiazolin-5-one, condensation with acetonedicarboxylic acid monomethyl ester-monoamide and subsequent epimerization with pyridine to give 4-de-dimethylamino-4-thiobenzamido-5,5-dimethyl-8-benzyloxy-10-0-benzyl-12a-dehydroxy-6-oxatetracycline and 12a-hydroxylation, splitting off the thiobenzoyl group and methylation].

EXAMPLE 15

A mixture of 523 mg of $N_{(2)}$-tert.-butyl-7-chloro-6-thiatetracycline, 10 ml of 48% HBr and 15 ml of acetic acid is heated at 100° for 15 minutes. After working up with water and n-butanol, 7-chloro-6-thiatetracycline is obtained; m.p. 223°.

The starting material can be obtained by condensation of 2-phenyl-4-[2-(5-hydroxy-8-chloro-thiochroman-4-on-2-yl)-ethylidene]-2-thiazolin-5-one with acetonedicarboxylic acid monomethyl ester-mono-N-tert.-butylamide to give a mixture of stereoisomeric 4-thiobenzamido-1,4,4a,5,5a,6,11,12a-octahydro-3,10,12-trihydroxy-7-chloro-1,11-dioxo-6-thianaphthacene-2-N-tert.-butyl-carboxamides, epimerisation with pyridine to give $N_{(2)}$-tert.-butyl-4-de-dimethylamino-4-thiobenzamido-7-chloro-12a-dehydroxy-6-thiatetracycline, hydroxylation to give $N_{(2)}$-tert.-butyl-4-de-dimethylamino-4-thiobenzamido-7-chloro-6-thiatetracycline, reaction with fluorosulphonic acid methyl ester to give the methylimino-thioether, hydrolysis to give the 4-amino compound (analogously to Example 1) and methylation analogously to Example 18.

EXAMPLE 16

200 mg of 7-chloro-12a-dehydroxy-6-thiatetracycline are dissolved in 150 ml of methanol and a solution of 175 mg of Cer(III) chloride in 85 ml of methanol is added, while stirring. 2.35 ml of a buffer solution (prepared from 38.3 ml of 0.1 N NaOH and 61.7 ml of an aqueous solution which contains 7.505 g of glycine and 5.85 g of NaCl per liter) are added to the resulting mixture. Oxygen is then passed into the mixture of 12 hours and the solution is concentrated to about 50 ml and worked up with hydrochloric acid and chloroform to give 7-chloro-6-thiatetracycline; m.p. 223°.

The starting material can be prepared from 4-de-dimethylamino-4-thiobenzamido-7-chloro-12a-dehydroxy-6-thiatetracycline by hydrolysis to give 4-de-dimethylamino-4-amino-7-chloro-12a-dehydroxy-6-thiatetracycline and subseuent methylation.

EXAMPLE 17

467 mg of 6-acetyl-6-azatetracycline are heated with 10 ml of 48% hydrobromic acid and 15 ml of acetic acid for 6 hours at 90° and the mixture is washed with chloroform and extracted with n-butanol. After filtering through silica gel and evaporating, 6azatetracycline is obtained.

5a-epi-6-azatetracycline,
4-de-dimethylamino-4-amino-6-azatetracycline and
4-de-dimethylamino-4-amino-5a-epi-6-azatetracycline are obtained analogously from the corresponding 6-acetyl compounds.

EXAMPLE 18

400 mg of sodium cyanoborohydride, 0.5 ml of 35% aqueous formaldehyde solution and a little sodium sulfate are added to a solution of 439 mg of 4-de-dimethylamino-4-amino-7-chloro-6-thiatetracycline (obtained in accordance with Example 1) in 80 ml of methanol and the mixture is stirred for 30 minutes at 20°. Chloroform is then added and the chloroform solution is washed with dilute hydrochloric acid, dried and evaporated. This gives 7-chloro-6-thiatetracycline; m.p. 223°.

5-Methyl-7-chloro-6-thiatetracycline,
5-ethyl-7-chloro-6-thiatetracycline,
5-n-propyl-7-chloro-6-thiatetracycline,
5-n-butyl-7-chloro-6-thiatetracycline,
5,5-dimethyl-7-chloro-6-thiatetracycline,
5-methyl-5-ethyl-7-chloro-6-thiatetracycline,
5,5-diethyl-7-chloro-6-thiatetracycline,
6-thiatetracycline,
7-fluoro-6-thiatetracycline,
8-fluoro-6-thiatetracycline,
9-fluoro-6-thiatetracycline,
8-chloro-6-thiatetracycline,
9-chloro-6-thiatetracycline,
7-bromo-6-thiatetracycline,
8-bromo-6-thiatetracycline,
9-bromo-6-thiatetracycline,
7-trifluoromethyl-6-thiatetracycline,
8-trifluoromethyl-6-thiatetracycline,
9-trifluoromethyl-6-thiatetracycline,
7-hydroxy-6-thiatetracycline,
8-hydroxy-6-thiatetracycline,
9-hydroxy-6-thiatetracycline,
7-methyl-6-thiatetracycline,
8-methyl-6-thiatetracycline,
9-methyl-6-thiatetracycline,
8-methoxy-6-thiatetracycline, m.p. 215°–218°
9-methoxy-6-thiatetracycline,
7-ethoxy-6-thiatetracycline,
8-ethoxy-6-thiatetracycline,
9-ethoxy-6-thiatetracycline,
7-dimethylamino-6-thiatetracycline,
8-dimethylamino-6-thiatetracycline,
9-dimethylamino-6-thiatetracycline,
7-acetamido-6-thiatetracycline,
8-acetamido-6-thiatetracycline,
9-acetamido-6-thiatetracycline,
6-methyl-6-azatetracycline,
6-methyl-7-fluoro-6-azatetracycline,
6-methyl-8-fluoro-6-azatetracycline,
6-methyl-9-fluoro-6-azatetracycline,
6methyl-7-chloro-6-azatetracycline,
6-methyl-8-chloro-6-azatetracycline,
6-methyl-9-chloro-6-azatetracycline,
6-methyl-7-bromo-6-azatetracycline,
6-methyl-8-bromo-6-azatetracycline,
6-methyl-9-bromo-6-azatetracycline,
6-methyl-7-trifluoromethyl-6-azatetracycline,
6-methyl-8-trifluoromethyl-6-azatetracycline,
6-methyl-9-trifluoromethyl-6-azatetracycline,
6-methyl-7-hydroxy-6-azatetracycline,
6-methyl-8-hydroxy-6-azatetracycline,
6-methyl-9-hydroxy-6-azatetracycline,
6,7-dimethyl-6-azatetracycline,
6,8-dimethyl-6-azatetracycline,
6,9-dimethyl-6-azatetracycline,
6-methyl-7-methoxy-6-azatetracycline,
6-methyl-8-methoxy-6-azatetracycline,
6-methyl-9-methoxy-6-azatetracycline,
6-methyl-7-ethoxy-6-azatetracycline,
6-methyl-8-ethoxy-6-azatetracycline,
6-methyl-9-ethoxy-6-azatetracycline,
6-methyl-7-dimethylamino-6-azatetracycline,
6-methyl-8-dimethylamino-6-azatetracycline,
6-methyl-9-dimethylamino-6-azatetracycline,
6-methyl-7-acetamido-6-azatetracycline,
6-methyl-8-acetamido-6-azatetracycline.
6-methyl-9-acetamido-6-azatetracycline,
6-acetyl-6-azatetracycline,
6-acetyl-7-fluoro-6-azatetracycline,
6-acetyl-8-fluoro-6-azatetracycline,
6-acetyl-9-fluoro-6-azatetracycline,
6-acetyl-7-chloro-6-azatetracycline,
6-acetyl-8-chloro-6-azatetracycline,
6-acetyl-9-chloro-6-azatetracycline,
6-acetyl-7-bromo-6-azatetracycline,
6-acetyl-8-bromo-6-azatetracycline,
6-acetyl-9-bromo-6-azatetracycline,
6-acetyl-7-trifluoromethyl-6-azatetracycline,
6-acetyl-8-trifluoromethyl-6-azatetracycline,
6-acetyl-9-trifluoromethyl-6-azatetracycline, 6-acetyl-7-hydroxy-6-azatetracycline,
6-acetyl-8-hydroxy-6-azatetracycline,
6-acetyl-9-hydroxy-6-azatetracycline,
6-acetyl-7-methyl-6-azatetracycline,
6-acetyl-8-methyl-6-azatetracycline,
6-acetyl-9-methyl-6-azatetracycline,
6-acetyl-7-methoxy-6-azatetracycline,
6-acetyl-8-methoxy-6-azatetracycline,
6-acetyl-9-methoxy-6-azatetracycline,
6-acetyl-7-ethoxy-6-azatetracycline,
6-acetyl-8-ethoxy-6-azatetracycline,
6-acetyl-9-ethoxy-6-azatetracycline,
6-acetyl-7-dimethylamino-6-azatetracycline,
6-acetyl-8-dimethylamino-6-azatetracycline,
6-acetyl-9-dimethylamino-6-azatetracycline,
6-acetyl-7-acetamido-6-azatetracycline,
6-acetyl-8-acetamido-6-azatetracycline,
6-acetyl-9-acetamido-6-azatetracycline,
6-oxatetracycline,
7-fluoro-6-oxatetracycline,
8-fluoro-6-oxatetracycline,
9-fluoro-6-oxatetracycline,
7-chloro-6-oxatetracycline,
8-chloro-6-oxatetracycline,
9-chloro-6-oxatetracycline,
7-bromo-6-oxatetracycline,
8-bromo-6-oxatetracycline,
9-bromo-6-oxatetracycline,
7-trifluoromethyl-6-oxatetracycline,
8-trifluoromethyl-6-oxatetracycline,
9-trifluoromethyl-6-oxatetracycline,
7-hydroxy-6-oxatetracycline,
8-hydroxy-6-oxatetracycline,
9-hydroxy-6-oxatetracycline,
7-methyl-6-oxatetracycline,
8-methyl-6-oxatetracycline,
9-methyl-6-oxatetracycline,
7-methoxy-6-oxatetracycline,
8-methoxy-6-oxatetracycline,
9-methoxy-6-oxatetracycline,
7-ethoxy-6-oxatetracycline,
8-ethoxy-6-oxatetracycline,
9-ethoxy-6-oxatetracycline,
7-dimethylamino-6-oxatetracycline,
8-dimethylamino-6-oxatetracycline,
9-dimethylamino-6-oxatetracycline,
7-acetamido-6-oxatetracycline,
8-acetamido-6-oxatetracycline,
9-acetamido-6-oxatetracycline,
5,5-dimethyl-6-oxatetracycline,
5,5-dimethyl-7-fluoro-6-oxatetracycline,
5,5-dimethyl-8-fluoro-6-oxatetracycline,
5,5-dimethyl-9-fluoro-6-oxatetracycline,
5,5-dimethyl-7-chloro-6-oxatetracycline,
5,5-dimethyl-8-chloro-6-oxatetracycline,
5,5-dimethyl-9-chloro-6-oxatetracycline,
5,5-dimethyl-7-bromo-6-oxatetracycline,
5,5-dimethyl-8-bromo-6-oxatetracycline,
5,5-dimethyl-9-bromo-6-oxatetracycline,
5,5-dimethyl-7-trifluoromethyl-6-oxatetracycline,
5,5-dimethyl-8-trifluoromethyl-6-oxatetracycline,
5,5-dimethyl-9-trifluoromethyl-6-oxatetracycline,
5,5-dimethyl-7-hydroxy-6-oxatetracycline,
5,5-dimethyl-8-hydroxy-6-oxatetracycline,
5,5-dimethyl-9-hydroxy-6-oxatetracycline,
5,5,7-trimethyl-6-oxatetracycline,
5,5,8-trimethyl-6-oxatetracycline,
5,5,9-trimethyl-6-oxatetracycline,
5,5-dimethyl-7-methoxy-6-oxatetracycline,
5,5-dimethyl-8-methoxy-6-oxatetracycline,
5,5-dimethyl-9-methoxy-6-oxatetracycline,
5,5-dimethyl-7-ethoxy-6-oxatetracycline,
5,5-dimethyl-8-ethoxy-6-oxatetracycline,
5,5-dimethyl-9-ethoxy-6-oxatetracycline,
5,5-dimethyl-7-dimethylamino-6-oxatetracycline,
5,5-dimethyl-8-dimethylamino-6-oxatetracycline,
5,5-dimethyl-9-dimethylamino-6-oxatetracycline,
5,5-dimethyl-7-acetamido-6-oxatetracycline,
5,5-dimethyl-8-acetamido-6-oxatetracycline and
5,5-dimethyl-9-acetamido-6-oxatetracycline as well as the corresponding 5a-epi-compounds, for example, 7-chloro-5a-epi-6-thiatetracycline, m.p. 216°–27°;
8-methoxy-5a-epi-6-thiatetracycline,
7-dimethylamino-5-epi-6-thiatetracycline,
7-acetamido-5a-epi-6-thiatetracycline
6-methyl-5a-epi-6-azatetracycline,
6-acetyl-5a-epi-6-azatetracycline and
5,5-dimethyl-8-methoxy-5a-epi-6-oxatetracycline, can be obtained analogously by methylation.

EXAMPLE 19

439 mg of 4-de-dimethylamino-4-amino-7-chloro-6-thiatetracycline and 0.5 ml of 35% aqueous formaldehyde solution are dissolved in 80 ml of methanol, 100 mg of 5% Pd-on-charcoal are added to the solution and hydrogenation is carried out at 20° and normal pressure until saturation is reached. After filtering and evaporating, 7-chloro-6-thiatetracycline is obtained; m.p. 223°.

4-De-dimethylamino-4-diethylamino-7-chloro-6-thiatetracycline, m.p. 190°–192°
4-de-dimethylamino-4-di-n-propylamino-7-chloro-6-thiatetracycline,
4-de-dimethylamino-4-diisopropylamino-7-chloro-6-thiatetracycline,
4-de-dimethylamino-4-di-n-butylamino-7-chloro-6-thiatetracycline,
4-de-dimethylamino-4-diisobutylamino-7-chloro-6-thiatetracycline and
4-de-dimethylamino-4-di-sec.-butylamino-7-chloro-6-thiatetracycline are obtained analogously using the corresponding aldehydes and ketones.

EXAMPLE 20 a. 476 mg of 4-de-dimethylamino-4-amino-7-chloro-6-thiatetracycline hydrochloride (obtained in accordance with Example 1) are dissolved in 20 ml of formic acid, 0.95 g of the mixed anhydride of formic acid and acetic acid and 70 mg of sodium formate are added and the mixture is stirred for 24 hours at 20°. After evaporation 4-de-dimethylamino-4-formamido-7-chloro-6-thiatetracycline is obtained.

b. 467 mg of 4-de-dimethylamino-4-formamido-7-chloro-6-thiatetracycline are stirred with 400 mg of sodium cyano borohydride in 80 ml of methanol for 1 hour at 20° and the mixture is worked up with dilute hydrochloric acid and chloroform to give 4-de-dimethylamino-4-methylamino-7-chloro-6-thiotetracycline.

By successive acylation and reduction, corresponding 4-de-dimethylamino-4-alkylamino-6-thia-, -6-aza- and -6-oxa-tetracyclines and the corresponding 5a-epi-compounds are obtained analogously, in particular:

4-de-dimethylamino-4-methylamino-5-methyl-7-chloro-6-thiatetracycline,
4-de-dimethylamino-4-methylamino-5-ethyl-7-chloro-6-thiatetracycline,
4-de-dimethylamino-4-methylamino-5-n-propyl-7-chloro-6-thiatetracycline,
4-de-dimethylamino-4-methylamino-5-n-butyl-7-chloro-6-thiatetracycline,
4-de-dimethylamino-4-methylamino-5,5-dimethyl-7-chloro-6-thiatetracycline,
4-de-dimethylamino-4-methylamino-5-methyl-5-ethyl-7-chloro-6-thiatetracycline,
4-de-dimethylamino-4-methylamino-5,5-diethyl-7-chloro-6-thiatetracycline,
4-de-dimethylamino-4-methylamino-6-thiatetracycline,
4-de-dimethylamino-4-methylamino-7-fluoro-6-thiatetracycline,
4-de-dimethylamino-4-methylamino-8-fluoro-6-thiatetracycline,
4-de-dimethylamino-4-methylamino-9-fluoro-6-thiatetracycline,
4-de-dimethylamino-4-methylamino-8-chloro-6-thiatetracycline,
4-de-dimethylamino-4-methylamino-9-chloro-6-thiatetracycline,
4-de-dimethylamino-4-methylamino-7-bromo-6-thiatetracycline,
4-de-dimethylamino-4-methylamino-8-bromo-6-thiatetracycline,
4-de-dimethylamino-4-methylamino-9-bromo-6-thiatetracycline,
4-de-dimethylamino-4-methylamino-7-trifluoromethyl-6-thiatetracycline,
4-de-dimethylamino-4-methylamino-8-trifluoromethyl-6-thiatetracycline,
4-de-dimethylamino-4-methylamino-9-trifluoromethyl-6-thiatetracycline,
4-de-dimethylamino-4-methylamino-7hydroxy-6-thiatetracycline,
4-de-dimethylamino-4-methylamino-8-hydroxy-6-thiatetracycline,
4-de-dimethylamino-4-methylamino-9-hydroxy-6-thiatetracycline,
4-de-dimethylamino-4-methylamino-7-methyl-6-thiatetracycline,
4-de-dimethylamino-4-methylamino-8-methyl-6-thiatetracycline,
4-de-dimethylamino-4-methylamino-9-methyl-6-thiatetracycline,
4-de-dimethylamino-4-methylamino-8-methoxy-6-thiatetracycline,
4-de-dimethylamino-4-methylamino-9-methoxy-6-thiatetracycline,
4-de-dimethylamino-4-methylamino-7-ethoxy-6-thiatetracycline,
4-de-dimethylamino-4-methylamino-8-ethoxy-6-thiatetracycline,
4-de-dimethylamino-4-methylamino-9-ethoxy-6-thiatetracycline,
4-de-dimethylamino-4-methylamino-7-dimethylamino-6-thiatetracycline,
4-de-dimethylamino-4-methylamino-8-dimethylamino-6-thiatetracycline,
4-de-dimethylamino-4-methylamino-9-dimethylamino-6-thiatetracycline,
4-de-dimethylamino-4-methylamino-7-acetamido-6-thiatetracycline,
4-de-dimethylamino-4-methylamino-8-acetamido-6-thiatetracycline,
4-de-dimethylamino-4-methylamino-9-acetamido-6-thiatetracycline,
4-de-dimethylamino-4-methylamino-6-methyl-6-azatetracycline,
4-de-dimethylamino-4-methylamino-6-methyl-7-fluoro-6-azatetracycline,
4-de-dimethylamino-4-methylamino-6-methyl-8-fluoro-6-azatetracycline,
4-de-dimethylamino-4-methylamino-6-methyl-9-fluoro-6-azatetracycline,
4-de-dimethylamino-4-methylamino-6-methyl-7-chloro-6-azatetracycline,
4-de-dimethylamino-4-methylamino-6-methyl-8-chloro-6-azatetracycline,
4-de-dimethylamino-4-methylamino-6-methyl-9-chloro-6-azatetracycline,
4-de-dimethylamino-4-methylamino-6-methyl-7-bromo-6-azatetracycline,
4-de-dimethylamino-4-methylamino-6-methyl-8-bromo-6-azatetracycline,
4-de-dimethylamino-4-methylamino-6-methyl-9-bromo-6-azatetracycline,
4-de-dimethylamino-4-methylamino-6-methyl-7-trifluoromethyl-6-azatetracycline,
4-de-dimethylamino-4-methylamino-6-methyl-8-trifluoromethyl-6-azatetracycline,
4-de-dimethylamino-4-methylamino-6-methyl-9-trifluoromethyl-6-azatetracycline,
4-de-dimethylamino-4-methylamino-6-methyl-7-hydroxy-6-azatetracycline,
4-de-dimethylamino-4-methylamino-6-methyl-8-hydroxy-6-azatetracycline,
4-de-dimethylamino-4-methylamino-6-methyl-9-hydroxy-6-azatetracycline,
4-de-dimethylamino-4-methylamino-6,7-dimethyl-6-azatetracycline,
4-de-dimethylamino-4-methylamino-6,8-dimethyl-6-azatetracycline,
4-de-dimethylamino-4-methylamino-6,9-dimethyl-6-azatetracycline,
4-de-dimethylamino-4-methylamino-6-methyl-7-methoxy-6-azatetracycline,
4-de-dimethylamino-4-methylamino-6-methyl-8-methoxy-6-azatetracycline,
4-de-dimethylamino-4-methylamino-6-methyl-9-methoxy-6-azatetracycline,
4-de-dimethylamino-4-methylamino-6-methyl-7-ethoxy-6-azatetracycline,
4-de-dimethylamino-4-methylamino-6-methyl-8-ethoxy-6-azatetracycline,
4-de-dimethylamino-4-methylamino-6-methyl-9-ethoxy-6-azatetracycline,
4-de-dimethylamino-4-methylamino-6-methyl-7-dimethylamino-6-azatetracycline,
4-de-dimethylamino-4-methylamino-6-methyl-8-dimethylamino-6-azatetracycline,
4-de-dimethylamino-4-methylamino-6-methyl-9-dimethylamino-6-azatetracycline,
4-de-dimethylamino-4-methylamino-6-methyl-7-acetamido-6-azatetracycline,
4-de-dimethylamino-4-methylamino-6-methyl-8-acetamido-6-azatetracycline,
4-de-dimethylamino-4-methylamino-6-methyl-9-acetamido-6-azatetracycline, 4-de-dimethylamino-4-methylamino-6-acetyl-6-azatetracycline,
4-de-dimethylamino-4-methylamino-6-acetyl-7-fluoro-6-azatetracycline,
4-de-dimethylamino-4-methylamino-6-acetyl-8-fluoro-6-azatetracycline,
4-de-dimethylamino-4-methylamino-6-acetyl-9-fluoro-6-azatetracycline,
4-de-dimethylamino-4-methylamino-6-acetyl-7-chloro-6-azatetracycline,
4-de-dimethylamino-4-methylamino-6-acetyl-8-chloro-6-azatetracycline,
4-de-dimethylamino-4-methylamino-6-acetyl-9-chloro-6-azatetracycline,
4-de-dimethylamino-4-methylamino-6-acetyl-7-bromo-6-azatetracycline,
4-de-dimethylamino-4-methylamino-6-acetyl-8-bromo-6-azatetracycline,
4-de-dimethylamino-4-methylamino-6-acetyl-9-bromo-6-azatetracycline,
4-de-dimethylamino-4-methylamino-6-acetyl-7-trifluoromethyl-6-azatetracycline,
4-de-dimethylamino-4-methylamino-6-acetyl-8-trifluoromethyl-6-azatetracycline,
4-de-dimethylamino-4-methylamino-6-acetyl-9-trifluoromethyl-6-azatetracycline,
4-de-dimethylamino-4-methylamino-6-acetyl-7-hydroxy-6-azatetracycline,
4-de-dimethylamino-4-methylamino-6-acetyl-8-hydroxy-6-azatetracycline,
4-de-dimethylamino-4-methylamino-6-acetyl-9-hydroxy-6-azatetracycline,
4-de-dimethylamino-4-methylamino-6-acetyl-7-methyl-6-azatetracycline,
4-de-dimethylamino-4-methylamino-6-acetyl-8-methyl-6-azatetracycline,
4-de-dimethylamino-4-methylamino-6-acetyl-9-methyl-6-azatetracycline,
4-de-dimethylamino-4-methylamino-6-acetyl-7-methoxy-6-azatetracycline,
4-de-dimethylamino-4-methylamino-6-acetyl-8-methoxy-6-azatetracycline,
4-de-dimethylamino-4-methylamino-6-acetyl-9-methoxy-6-azatetracycline,
4-de-dimethylamino-4-methylamino-6-acetyl-7-ethoxy-6-azatetracycline,
4-de-dimethylamino-4-methylamino-6-acetyl-8-ethoxy-6-azatetracycline,
4-de-dimethylamino-4-methylamino-6-acetyl-9-ethoxy-6-azatetracycline,
4-de-dimethylamino-4-methylamino-6-acetyl-7-dimethylamino-6-azatetracycline,
4-de-dimethylamino-4-methylamino-6-acetyl-8-dimethylamino-6-azatetracycline,
4-de-dimethylamino-4-methylamino-6-acetyl-9-dimethylamino-6-azatetracycline,
4-de-dimethylamino-4-methylamino-6-acetyl-7-acetamido-6-azatetracycline,
4-de-dimethylamino-4-methylamino-6-acetyl-8-acetamido-6-azatetracycline,
4-de-dimethylamino-4-methylamino-6-acetyl-9-acetamido-6-azatetracycline,
4-de-dimethylamino-4-methylamino-6-oxatetracycline,
4-de-dimethylamino-4-methylamino-7-fluoro-6-oxatetracycline,
4-de-dimethylamino-4-methylamino-8-fluoro-6-oxatetracycline,
4-de-dimethylamino-4-methylamino-9-fluor-6-oxatetracycline,
4-de-dimethylamino-4-methylamino-7-chloro-6-oxatetracycline,
4-de-dimethylamino-4-methylamino-8-chloro-6-oxatetracycline,
4-de-dimethylamino-4-methylamino-9-chloro-6-oxatetracycline,
4-de-dimethylamino-4-methylamino-7-bromo-6-oxatetracycline,
4-de-dimethylamino-4-methylamino-8-bromo-6-oxatetracycline,
4-de-dimethylamino-4-methylamino-9-bromo-6-oxatetracycline,
4-de-dimethylamino-4-methylamino-7-trifluoromethyl-6-oxatetracycline,
4-de-dimethylamino-4-methylamino-8-trifluoromethyl-6-oxatetracycline,
4-de-dimethylamino-4-methylamino-9-trifluoromethyl-6-oxatetracycline,
4-de-dimethylamino-4-methylamino-7-hydroxy-6-oxatetracycline,
4-de-dimethylamino-4-methylamino-8-hydroxy-6-oxatetracycline,
4-de-dimethylamino-4-methylamino-9-hydroxy-6-oxatetracycline,
4-de-dimethylamino-4-methylamino-7-methyl-6-oxatetracycline,
4-de-dimethylamino-4-methylamino-8-methyl-6-oxatetracycline,
4-de-dimethylamino-4-methylamino-9-methyl-6-oxatetracycline,
4-de-dimethylamino-4-methylamino-7-methoxy-6-oxatetracycline,
4-de-dimethylamino-4-methylamino-8-methoxy-6-oxatetracycline,
4-de-dimethylamino-4-methylamino-9-methoxy-6-oxatetracycline,
4-de-dimethylamino-4-methylamino-7-ethoxy-6-oxatetracycline,
4-de-dimethylamino-4-methylamino-8-ethoxy-6-oxatetracycline,
4-de-dimethylamino-4-methylamino-9-ethoxy-6-oxatetracycline,
4-de-dimethylamino-4-methylamino-7-dimethylamino-6-oxatetracycline,
4-de-dimethylamino-4-methylamino-8-dimethylamino-6-oxatetracycline,
4-de-dimethylamino-4-methylamino-9-dimethylamino-6-oxatetracycline,
4-de-dimethylamino-4-methylamino-7-acetamido-6-oxatetracycline,
4-de-dimethylamino-4-methylamino-8-acetamido-6-oxatetracycline,
4-de-dimethylamino-4-methylamino-9-acetamido-6-oxatetracycline,
4-de-dimethylamino-4-methylamino-5,5-dimethyl-6-oxatetracycline,
4-de-dimethylamino-4-methylamino-5,5-dimethyl-7-fluoro-6-oxatetracycline,
4-de-dimethylamino-4-methylamino-5,5-dimethyl-8-fluoro-6-oxatetracycline,
4-de-dimethylamino-4-methylamino-5,5-dimethyl-9-fluoro-6-oxatetracycline,
4-de-dimethylamino-4-methylamino-5,5-dimethyl-7-chloro-6-oxatetracycline,
4-de-dimethylamino-4-methylamino-5,5-dimethyl-8-chloro-6-oxatetracycline, 4-de-dimethylamino-4-methylamino-5,5-dimethyl-9-chloro-6-oxatetracycline,
4-de-dimethylamino-4-methylamino-5,5-dimethyl-7-bromo-6-oxatetracycline,
4-de-dimethylamino-4-methylamino-5,5-dimethyl-8-bromo-6-oxatetracycline,
4-de-dimethylamino-4-methylamino-5,5-dimethyl-9-bromo-6-oxatetracycline,
4-de-dimethylamino-4-methylamino-5,5-dimethyl-7-trifluoromethyl-6-oxatetracycline,
4-de-dimethylamino-4-methylamino-5,5-dimethyl-8-trifluoromethyl-6-oxatetracycline,
4-de-dimethylamino-4-methylamino-5,5-dimethyl-9-trifluoromethyl-6-oxatetracycline,
4-de-dimethylamino-4-methylamino-5,5-dimethyl-7-hydroxy-6-oxatetracycline,
4-de-dimethylamino-4-methylamino-5,5-dimethyl-8-hydroxy-6-oxatetracycline,
4-de-dimethylamino-4-methylamino-5,5-dimethyl-9-hydroxy-6-oxatetracycline,
4-de-dimethylamino-4-methylamino-5,5,7-trimethyl-6-oxatetracycline,
4-de-dimethylamino-4-methylamino-5,5,8-trimethyl-6-oxatetracycline,
4-de-dimethylamino-4-methylamino-5,5,9-trimethyl-6-oxatetracycline,
4-de-dimethylamino-4-methylamino-5,5-dimethyl-7-methoxy-6-oxatetracycline,
4-de-dimethylamino-4-methylamino-5,5-dimethyl-8-methoxy-6-oxatetracycline,
4-de-dimethylamino-4-methylamino-5,5-dimethyl-9-methoxy-6-oxatetracycline,
4-de-dimethylamino-4-methylamino-5,5-dimethyl-7-ethoxy-6-oxatetracycline,
4-de-dimethylamino-4-methylamino-5,5-dimethyl-8-ethoxy-6-oxatetracycline,
4-de-dimethylamino-4-methylamino-5,5-dimethyl-9-ethoxy-6-oxatetracycline,
4-de-dimethylamino-4-methylamino-5,5-dimethyl-7-dimethylamino-6-oxatetracycline,
4-de-dimethylamino-4-methylamino-5,5-dimethyl-8-dimethylamino-6-oxatetracycline,
4-de-dimethylamino-4-methylamino-5,5-dimethyl-9-dimethylamino-6-oxatetracycline,
4-de-dimethylamino-4-methylamino-5,5-dimethyl-7-acetamido-6-oxatetracycline,
4-de-dimethylamino-4-methylamino-5,5-dimethyl-8-acetamido-6-oxatetracycline and
4-de-dimethylamino-4-methylamino-5,5-dimethyl-9-acetamido-6-oxatetracycline as well as the corresponding 5a-epi-compounds, for example 4-de-dimethylamino-4-methylamino-7-chloro-5a-epi-6-thiatetracycline,
4-de-dimethylamino-4-methylamino-8-methoxy-5a-epi-6-thiatetracycline,
4-de-dimethylamino-4-methylamino-7-dimethylamino-5a-epi-6-thiatetracycline,
4-de-dimethylamino-4-methylamino-7-acetamido-5a-epi-6-thiatetracycline,
4-de-dimethylamino-4-methylamino-6-methyl-5a-epi-6-azatetracycline,
4-de-dimethylamino-4-methylamino-6-acetyl-5a-epi-6-azatetracycline and
4-de-dimethylamino-4-methylamino-5,5-dimethyl-8-methoxy-5a-epi-6-oxatetracycline.

EXAMPLE 21

425 mg of 6-azatetracycline are dissolved in 20 ml of acetone, 0.5 ml of dimethyl sulfate and 200 mg of $K_2CO_3$ are added and the mixture is stirred for 48 hours at 20°. After working up in the customary manner, 6-methyl-6-azatetracycline is obtained.

6-Ethyl-6-azatetracycline, 6-n-propyl-6-azatetracycline, 6-isopropyl-6-azatetracycline, 6-n-butyl-6-azatetracycline and 6-isobutyl-6-azatetracycline as well as the corresponding 5a-epi-compounds are obtained analogously.

EXAMPLE 22

A mixture of 448 mg of 4-de-dimethylamino-4-amino-8-nitro-6-thiatetracycline, 252 mg of dimethyl sulphate, 258 mg of N-ethyl-N,N-diisopropylamine and 25 ml of dioxan is left to stand for 12 hours at 20°. It is worked up in the customary manner to give 8-nitro-6-thiatetracycline.

7-Nitro-6-thiatetracycline,
9-nitro-6-thiatetracycline,
7-nitro-6-oxatetracycline,
8-nitro-6-oxatetracycline,
9-nitro-6-oxatetracycline,
5,5-dimethyl-7-nitro-6-oxatetracycline,
5,5-dimethyl-8-nitro-6-oxatetracycline,
5,5-dimethyl-9-nitro-6-oxatetracycline,
6-methyl-7-nitro-6-azatetracycline,
6-methyl-8-nitro-6-azatetracycline,
6-methyl-9-nitro-6-azatetracycline,
6-acetyl-7-nitro-6-azatetracycline,
6-acetyl-8-nitro-6-azatetracycline and
6-acetyl-9-nitro-6-azatetracycline as well as the corresponding 5a-epi-compounds, for example
5a-epi-8-nitro-6-thiatetracycline, are obtained analogously by methylation.

EXAMPLE 23

10 ml of a 0.1 molar solution of diazomethane in dioxan are added to a solution of 448 mg of 8-hydroxy-6-thiatetracycline in 20 ml of dioxane and the mixture is left to stand for one hour at 20° and evaporated. This gives 8-methoxy-6-thiatetracycline.

EXAMPLE 24

425 mg of 6-azatetracycline are allowed to stand overnight at 20° with 5 ml of propionic anhydride and 5 ml of pyridine, the mixture is poured into water and extracted with n-butanol and after the customary working up 6-propionyl-6-azatetracycline is obtained.

6-Butyryl-6-azatetracycline and 6-isobutyryl-6-azatetracycline as well as the corresponding 5a-epi-compounds are obtained analogously.

EXAMPLE 25

A solution of 0.11 ml of 30% $H_2O_2$ in 7 ml of acetic acid is added to a solution of 467 mg of 7-chloro-6-thiatetracycline in 10 ml of acetic acid and the mixture is left to stand for 24 hours at 20°. It is then poured into water and extracted with n-butanol and after the customary working up 7-chloro-6-thiatetracycline-6-oxide is obtained.

EXAMPLE 26

2.3 ml of 30% $H_2O_2$ are added to a warm solution of 4.67 g of 7-chloro-6-thiatetracycline in 100 ml of acetic acid and the mixture is boiled for 30 minutes. It is poured into water and extracted with n-butanol and after the customary working up 7-chloro-6-thiatetracycline-6,6-dioxide is obtained.

EXAMPLE 27

432 mg of 6-thiatetracycline are dissolved in 4 ml of liquid HF, the solution is cooled to −78° and 101 mg of $KNO_3$ are added and the mixture is warmed for 30 minutes on a water bath, under $N_2$. The mixture is evaporated, the residue is taken up in acetone, the solution is filtered and the filtrate is poured into ether. The crude product which has precipitated is separated chromatographically on silica gel. This gives 9-nitro-6-thiatetracycline and 7-nitro-6-thiatetracycline.

EXAMPLE 28

A solution of 477 mg of 8-nitro-6-thiatetracycline in 25 ml of ethanol is hydrogenated on 300 mg of 10% Pd-on-charcoal at 20° and normal pressure until the reaction has ceased. After filtering and evaporating, 8-amino-6-thiatetracycline is obtained.

7-Amino-6-thiatetracycline,
9-amino-6-thiatetracycline,
7-amino-6-oxatetracycline,
8-amino-6-oxatetracycline,
9-amino-6-oxatetracycline,
5,5-dimethyl-7-amino-6-oxatetracycline,
5,5-dimethyl-8-amino-6-oxatetracycline,
5,5-dimethyl-9-amino-6-oxatetracycline,
6-methyl-7-amino-6-azatetracycline,
6-methyl-8-amino-6-azatetracycline,
6-methyl-9-amino-6-azatetracycline,
6-acetyl-7-amino-6-azatetracycline,
6-acetyl-8-amino-6-azatetracycline and
6-acetyl-9-amino-6-azatetracycline, as well as the corresponding 5a-epi-compounds, for example, 5a-epi-8-amino-6-thiatetracycline, are obtained analogously from the corresponding nitro compounds.

EXAMPLE 29

467 mg of 7-chloro-6-thiatetracycline in 25 ml of methanol are hydrogenated in the presence of 101 mg of triethylamine on 200 mg of 10% Pd-on-charcoal at 20° and normal pressure to give 6-thiatetracycline.

EXAMPLE 30

100 mg of a mixture of stereoisomeric 4-dimethylamino-1,4,4a,5,5a,6,11,12a-octahydro-3,10,12,12a-tetrahydroxy-7-chloro-1,11-dioxo-6-thianaphthacene-2-carboxamides (obtainable from the mixture of 4-thiobenzamido-1,4,4a,5,5a,6,11,12a-octahydro-3,10,12-trihydroxy-7-chloro-1,11-dioxo-6-thianaphthacene-2-carboxamides mentioned in Example 1, paragraph i) by means of successive 12-a-hydroxylation, hydrolysis analogously to Example 1 and methylation analogously to Example 18) are dissolved in a little n-butanol, a few drops of 1.5 N hydrochloric acid being added, 70 mg. of $CaCl_2$ and then 0.5 ml. of water are added to the solution and a 10% solution of ethanolamine in n-butanol is then added until a pH value of 8.5 is obtained and the mixture is boiled for 3.5 hours under $N_2$. After cooling, the mixture is worked up with 1 N hydrochloric acid and n-butanol. The crude product is chromatographed in chloroform on silica gel to give 7-chloro-6-thiatetracycline; m.p. 223°.

The examples which follow relate to pharmaceutical preparations which contain tetracyclic compounds of the general Formula I:

EXAMPLE A: TABLETS

A mixture consisting of 100 kg. of 7-chloro-6-thiatetracycline, 500 kg. of lactose, 180 kg. of potato starch, 10 kg. of magnesium stearate and 10 kg. of talc is pressed into tablets in the customary manner, each of which contains 100 mg. of the 7-chloro-6-thiatetracycline.

EXAMPLE B: DRAGEES

Tablets are formed analogously to Example A and subsequently are coated in the customary manner with a coating consisting of sugar, potato starch, talc and tragacanth.

EXAMPLE C: CAPSULES 50 kg. of 4-de-dimethylamino-4-amino-7-chloro-6-thiatetracycline are filled into hard gelatin capsules in the conventional manner, each of which contains 50 mg. of the active compound.

EXAMPLE D: CAPSULES

A pulverulent mixture, consisting of 250 kg. of 7-chloro-6-thiatetracycline, 2.5 kg. of finely divided silicic acid, 12.5 kg. of talc, 1.25 kg. of magnesium stearate, 2.5 kg. of vitamin $B_1$ chloride hydrochloride, 2.5 kg. of lactoflavin, 25 kg. of calcium D-pantothenate, 4 kg. of folic acid, 3 g. of cyanocobalamine and 84 kg. of sodium ascorbate, is filled into hard gelatin capsules in the conventional manner, each of which contains 250 mg. of the antibiotic.

Tablets, dragees and capsules which contain one or more of another compound of Formula I, or their physiologically acceptable salts, are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A tetracyclic compound of the formula

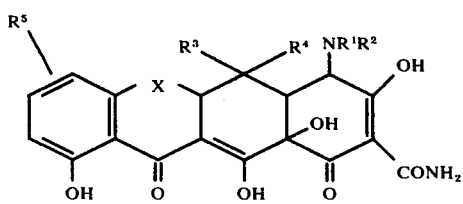

wherein $R^1$, $R^2$, $R^3$ and $R^4$ in each case are H or alkyl; $R^5$ is H, F, Cl, Br, $CF_3$, OH, alkyl, $NO_2$, $NH_2$, alkylamino, dialkylamino or alkanoylamino; and X is S, SO, or $SO_2$, alkyl and alkoxy in each instance being of 1–3 carbon atoms and alkanoyl being of 1–4 carbon atoms; and their physiologically acceptable acid addition salts.

2. A compound of claim 1, wherein $R^1$ and $R^2$ both are H or both are methyl and $R^3$ and $R^4$ both are hydrogen atoms or methyl groups in the syn configuration.

3. A compound of claim 1, wherein $R^3$ and $R^4$ each are hydrogen atoms in the anti-configuration.

4. A compound of claim 1, wherein X is S.

5. A compound of claim 2, wherein X is S.

6. A compound of claim 3, wherein X is S.

7. A compound of claim 1 selected from the group consisting of 4-de-dimethylamino-4-amino-6-thiatetracycline,
4-de-dimethylamino-4-amino-7-chloro-6-thiatetracycline,
4-de-dimethylamino-4-amino-8-hydroxy-6-thiatetracycline,
4-de-dimethylamino-4-amino-7-dimethylamino-6-thiatetracycline,
4-de-dimethylamino-4-amino-5a-epi-6-thiatetracycline,
4-de-dimethylamino-4-amino-7-chloro-5a-epi-6-thiatetracycline,
4-de-dimethylamino-4-amino-8-hydroxy-5a-epi-6-thiatetracycline,
4-de-dimethylamino-4-amino-7-dimethylamino-5a-epi-6-thiatetracycline,
6-thiatetracycline,
7-chloro-6-thiatetracycline,
8-hydroxy-6-thiatetracycline,
7-dimethylamino-6-thiatetracycline,
5a-epi-6-thiatetracycline,
7-chloro-5a-epi-6-thiatetracycline,
8-hydroxy-5a-epi-6-thiatetracycline, and
7-dimethylamino-5a-epi-6-thiatetracycline.

8. The compound of claim 1, 7-chloro-6-thiatetracycline.

9. The compound of claim 1, 4-de-dimethylamino-4-amino-7-chloro-6-thiatetracycline.

10. A pharmaceutical composition adapted for the treatment of bacterial infections and in unit dosage form, comprising an antibacterially effective amount per unit dosage of a compound of claim 1, in admixture with a pharmaceutically acceptable carrier.

11. A method of treating bacterial infections which comprises administering to the infected patient an antibacterially effective amount of a compound of claim 1.

12. A compound of the formula wherein $R^1$, $R^2$, $R^3$ and $R^4$ in each case are H or alkyl; $R^5$ is H, F, Cl, Br, $CF_3$, OH, alkyl, $No_2$, $NH_2$, alkylamino, dialkylamino or alkanoylamino; and X is S, SO, or $SO_2$, alkyl and alkoxy in each instance being of 1–3 carbon atoms and alkanoyl being of 1–4 carbon atoms; and their physiologically acceptable acid addition salts.

13. A compound of the formula wherein $R^3$ and $R^4$ are H or alkyl; $R^5$ is H,F,Cl, Br, $CR_3$, OH, alkyl, alkoxy, $NO_2$, $NH_2$, alkylamino, dialkylamino, or alkanoylamino; $R^6$ is H, SH, alkyl mercapto of 1–4 carbon atoms, benzyl mercapto, alkyl of 1–10 carbon atoms, phenyl, benzyl, phenoxymethyl, phenoxypropyl or the corresponding aryl group, mono- or disubstituted on the phenyl group by alkyl of 1–4 carbon atoms, OH, $OR^8$ wereiñ $R^8$ is alkyl, alkoxymethyl or acyl, each of up to 5 carbon atoms, tetrahydropyranyl, carbobenzoxy or benzyl; X is S, SO, or $SO_2$; Y is O or S, alkyl, alkoxy and alkanoyl in each case each being of 1–4 carbon atoms unless otherwise indicated; and $R^{11}$ is H or alkyl of 1–6 carbon atoms.

14. A compound of claim 1, 6-thiatetracycline.

15. The compound of claim 1, 7-dimethylamino-6-thiatetracycline.

16. A tetracyclic compound of the formula wherein $R^1$, $R^2$, $R^3$ and $R^4$ in each case are H or alkyl; $R^5$ is 8-methoxy or 9-methoxy and X is S, alkyl in each instance being of 1–3 carbon atoms; and their physiologically acceptable acid addition salts.

17. The compound of claim 16, 4-de-dimethylamino-4-amino-8-methoxy-6-thiatetracycline.

18. The compound of claim 16, 4-de-dimethylamino-4-amino-8-methoxy-5a-epi-6-thiatetracycline.

19. The compound of claim 16, 8-methoxy-5a-epi-6-thiatetracycline.

20. A compound of claim 16, 8-methoxy-6-thiatetracycline.

* * * * *

UNITED STATES PATENT AND TRADEMARK OFFICE
CERTIFICATE OF CORRECTION

PATENT NO. : 4,024,272
DATED : May 17, 1977
INVENTOR(S) : WERNER ROGALSKI ET AL.

It is certified that error appears in the above-identified patent and that said Letters Patent are hereby corrected as shown below:

Claim 13, Column 38, Line 19, should read

--- wherein $R^3$ and $R^4$ are H or alkyl; $R^5$ is H, F, Cl, Br, $CF_3$ ---.

Signed and Sealed this twenty-sixth Day of July 1977

[SEAL]

Attest:

RUTH C. MASON
*Attesting Officer*

C. MARSHALL DANN
*Commissioner of Patents and Trademarks*